(12) United States Patent
Hacker et al.

(10) Patent No.: US 6,486,096 B1
(45) Date of Patent: Nov. 26, 2002

(54) HERBICIDAL COMPOSITIONS WITH ACYLATED AMINOPHENYLSULFONYLUREAS

(75) Inventors: Erwin Hacker, Hochheim; Hermann Bieringer, Eppstein; Gerhard Schnabel, Grosswallstadt, all of (DE)

(73) Assignee: Hoechst Schering AgrEvo GmbH, Berlin (DE)

( * ) Notice: Subject to any disclaimer, the term of this patent is extended or adjusted under 35 U.S.C. 154(b) by 0 days.

(21) Appl. No.: 09/371,355

(22) Filed: Aug. 10, 1999

(30) Foreign Application Priority Data

Aug. 13, 1998 (DE) .......................... 198 36 725
Apr. 30, 1999 (DE) .......................... 199 19 853

(51) Int. Cl.⁷ ...................... A01N 43/64; A01N 57/00; A01N 43/54; A01N 43/60
(52) U.S. Cl. ...................... 504/133; 504/128; 504/134; 504/136
(58) Field of Search .............. 504/136, 128, 504/133, 134

(56) References Cited

U.S. PATENT DOCUMENTS

| 5,449,812 A | 9/1995 | Geisler et al. | 548/365.4 |
| 5,480,912 A | 1/1996 | Schnabel et al. | 560/13 |
| 5,922,646 A * | 7/1999 | Schnabel | 504/214 |
| 5,990,047 A | 11/1999 | Hacker et al. | 504/134 |

FOREIGN PATENT DOCUMENTS

| CA | 2230113 | 3/1998 |
| DE | 196 42 082 | 4/1997 |
| DE | 196 42 082 | 4/1998 |
| DE | 19642082 | * 4/1998 |
| DE | 196 50 995 | 6/1998 |
| WO | WO 95/29899 | 11/1995 |
| WO | WO 96/14747 | 5/1996 |
| WO | WO 97/10714 | 3/1997 |

* cited by examiner

Primary Examiner—Alton Pryor
(74) Attorney, Agent, or Firm—Frommer Lawrence & Haug LLP

(57) ABSTRACT

Herbicide combinations which contain components (A) and (B) have synergistic herbicidal effects on:
(A) one or more herbicides of the formula (I) or their salts,

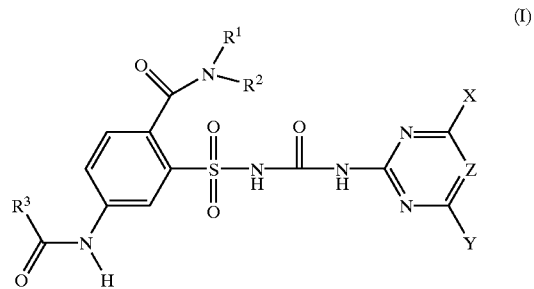

in which $R^1$, $R^2$, $R^3$, X, Y and Z are defined as in claim 1, and (B) one or more herbicides from the group of the compounds consisting of
(B1) foliar- and soil-acting herbicides which are effective selectively in cereals and some dicotyledonous crops against monocotyledonous and dicotyledonous harmful plants,
(B2) herbicides which are effective selectively in cereals and some dicotyledonous crops against predominantly dicotyledonous harmful plants and
(B3) herbicides which are to be employed nonselectively or in specifically tolerant crops and are effective against monocotyledonous and dicotyledonous harmful plants.

14 Claims, No Drawings

HERBICIDAL COMPOSITIONS WITH ACYLATED AMINOPHENYLSULFONYLUREAS

The invention is in the field of the crop protection products which can be employed against harmful plants in plant crops and which comprise, as herbicidally active substances, a combination of two or more herbicides.

The publication WO 95/M29899 discloses acylated aminophenylsulfonylureas and their salts, and their use as herbicides and/or plant growth regulators. Compounds of this structural class which are of particular interest are the compounds of the formula (I) and their salts

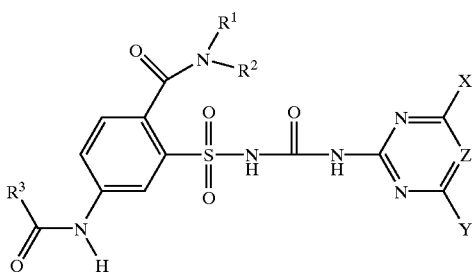

(I)

in which $R^1$ is hydrogen or $(C_1-C_4)$alkyl, preferably methyl or ethyl, in particular methyl, $R^2$ is hydrogen or $(C_1-C_4)$alkyl, preferably methyl or ethyl, in particular methyl, $R^3$ is H, $(C_1-C_4)$alkyl, $(C_1-C_4)$alkoxy, $(C_2-C_4)$alkenoxy, $(C_2-C_4)$alkynoxy, $(C_3-C_6)$cycloalkyl, each of the 5 last-mentioned radicals being unsubstituted or substituted by one or more radicals from the group consisting of halogen, cyano, $(C_1-C_4)$alkoxy and $(C_1-C_4)$alkylsulfonyl, preferably hydrogen, methyl, trifluoromethyl, ethyl, n-propyl, isopropyl, cyclopropyl, methoxy or ethoxy, preferably hydrogen, methyl or methoxy, in particular hydrogen, one of the radicals X and Y is halogen, $(C_1-C_4)$alkyl, $(C_1-C_4)$alkoxy, $(C_1-C_4)$alkylthio, where each of the three last-mentioned radicals is unsubstituted or substituted by one or more radicals from the group consisting of halogen, $(C_1-C_4)$alkoxy and $(C_1-C_4)$alkylthio, and the other of the radicals X and Y is $(C_1-C_4)$alkyl, $(C_1-C_4)$alkoxy or $(C_1-C_4)$alkylthio, where each of the three last-mentioned radicals is unsubstituted or substituted by one or more radicals from the group consisting of halogen, $(C_1-C_4)$alkoxy and $(C_1-C_4)$alkylthio, in particular X and Y are each methoxy, and Z is CH or N, in particular CH.

The efficacy of these herbicides against harmful plants in the plant crops is high, but generally depends on the application rate, the preparation in question, the harmful plants to be controlled or the harmful plant spectrum, the climatic conditions, the soil conditions etc. Another criterion is the duration of action, or the degradation rate of the herbicide. If appropriate, changes in the sensitivity of harmful plants, which may occur upon prolonged use of the herbicides or within a geographically limited area, must also be taken into consideration. The loss of action against individual plants can only be compensated for to some extent by higher application rates of the herbicides e.g. because the selectivity of the herbicides is thereby frequently adversely affected or improved efficacy is not achieved even at relatively high application rates. Sometimes, the selectivity in crops can be improved by the addition of safeners. In general, however, there is always a demand for methods to achieve the herbicidal effect with lower application rates of active substances. A lower application rate not only reduces the amount of an active substance required for application, but as a rule also reduces the amount of formulation auxiliaries required. Both reduce the economic outlay and improve the eco-friendliness of the herbicide treatment.

One possibility for improving the use profile of a herbicide may consist in combining the active substance with one or more other active substances which contribute the desired additional properties. However, the combined use of a plurality of active substances does not infrequently lead to phenomena of a physical and biological incompatibility, for example lacking stability of a coformulation, decomposition of an active substance or antagonism of the active substances. In contrast, what is desired are combinations of active substances with a favorable profile of action, high stability and as synergistic an increased action as possible, which allows the application rate to be reduced in comparison with the individual application of the active substances to be combined.

Surprisingly, it has now been found that active substances from the group of the abovementioned herbicides of the formula (I) or their salts in combination with specific structurally different herbicides interact especially favorably when they are employed in plant crops which are suitable for the selective use of the herbicides, if appropriate with the addition of safeners.

The invention therefore relates to herbicide combinations having an active content of components (A) and (B), wherein (A) is one or more herbicides from the group of the abovementioned compounds of formula (I) or their salts, and (B) is one or more herbicides from the group of the compounds which consists of (B1) foliar- and soil-acting herbicides which are effective selectively in cereals and some dicotyledonous crops against monocotyledonous and dicotyledonous harmful plants, (B2) herbicides which are effective selectively in cereals and some dicotyledonous crops against predominantly dicotyledonous harmful plants, and (B3) herbicides which are to be employed nonselectively or in specifically tolerant crops and are effective against monocotyledonous and dicotyledonous harmful plants.

The herbicide combinations according to the invention can contain other components, e.g. other types of crop protection active substances and/or adjuvants and/or formulation auxiliaries conventionally used in crop protection, or are used together with the latter.

The synergistic effects are observed when the active substances (A) and (B) are applied together, but can also frequently be observed upon split application (splitting). Another possibility is to apply the herbicides or herbicide combinations in several portions (sequential application), for example after pre-emergence applications, followed by post-emergence applications or after early post-emergence applications, followed by applications at medium or late post-emergence. Preferred is the simultaneous or nearly simultaneous application of the active substances of the combination in question.

The synergistic effects allow the application rates of the individual active substances to be reduced, a more potent action with the same application rate, the control of species to which the action has hitherto not extended (zero effect), an extended application period and/or a reduced number of required individual applications and—as a result for the user—economically and ecologically more advantageous weed control systems.

For example, the combinations of (A)+(B) according to the invention allow synergistically increased effects which far and unexpectedly exceed the effects which can be achieved with the individual active substances (A) and (B).

Said formula (I) encompasses all stereoisomers and their mixtures, in particular also racemic mixtures and—if enantiomers are possible—the particular enantiomer which has a biological action. Examples of active substances of the formula (I) are compounds of the formula (A1) and their salts

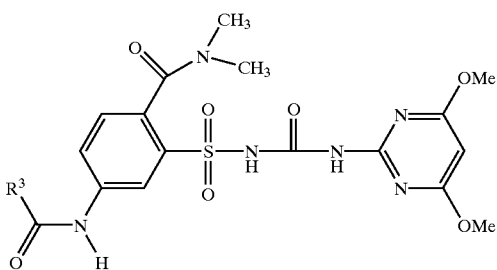

(A1)

in which $R^3$ is defined as in formula (I) and Me is methyl, preferably the compounds (A1.1) to (A1.6)

(A1.1) N-[N-(4,6-dimethoxypyrimidin-2-yl)aminocarbonyl]-2-(dimethylaminocarbonyl)-5-(formylamino)benzenesulfonamide, i.e. formula (A1) where $R^3$ = hydrogen, and its salts;
(A1.2) N-[N-(4,6-dimethoxypyrimidin-2-yl)aminocarbonyl]-2-(dimethylaminocarbonyl)-5-(acetylamino)benzenesulfonamide, i.e. formula (A1) where $R^3$ = methyl, and its salts;
(A1.3) N-[N-(4,6-dimethoxypyrimidin-2-yl)aminocarbonyl]-2-(dimethylaminocarbonyl)-5-(propionylamino)-benzenesulfonamide, i.e. formula (A1) where $R^3$ = ethyl, and its salts;
(A1.4) N-[N-(4,6-dimethoxypyrimidin-2-yl)aminocarbonyl]-2-(dimethylaminocarbonyl)-5-(isopropycarbonylamino)-benzenesulfonamide, i.e. formula (A1) where $R^3$ = isopropyl, and its salts;
(A1.5) N-[N-(4,6-dimethoxypyrimidin-2-yl)aminocarbonyl]-2-(dimethylaminocarbonyl)-5-(methoxycarbonylamino)-benzenesulfonamide, i.e. formula (A1) where $R^3$ = methoxy, and its salts;
(A1.6) N-[N-(4,6-dimethoxypyrimidin-2-yl)aminocarbonyl]-2-(dimethylaminocarbonyl)-5-(ethoxycarbonylamino)-benzenesulfonamide, i.e. formula (A1) where $R^3$ = ethoxy, and its salts.

Further examples of active compounds of the formula (I) are compounds of the formula (A2) and their salts

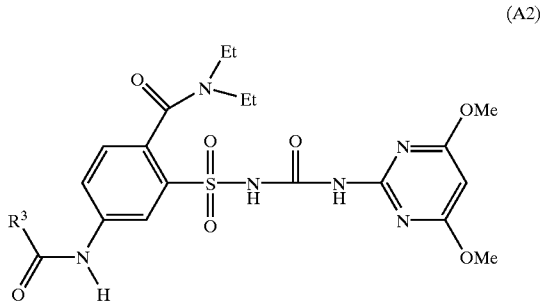

(A2)

in which $R^3$ is defined as in formula (I) and Me=methyl and Et=ethyl, preferably the compounds (A2.1) to (A2.6)

(A2.1) N-[N-(4,6-dimethoxypyrimidin-2-yl)aminocarbonyl]-2-(diethylaminocarbonyl)-5-(formylamino)benzenesulfonamide, i.e. formula (A2) where $R^3$ = hydrogen, and its salts;
(A2.2) N-[N-(4,6-dimethoxypyrimidin-2-yl)aminocarbonyl]-2-(diethylaminocarbonyl)-5-(acetylamino)benzenesulfonamide, i.e. formula (A2) where $R^3$ = methyl, and its salts;
(A2.3) N-[N-(4,6-dimethoxypyrimidin-2-yl)aminocarbonyl]-2-(diethylaminocarbonyl)-5-(propionylamino)benzenesulfonamide, i.e. formula (A2) where $R^3$ = ethyl, and its salts;
(A2.4) N-[N-(4,6-dimethoxypyrimidin-2-yl)aminocarbonyl]-2-(diethylaminocarbonyl)-5-(isopropylcarbonylamino)-benzenesulfonamide, i.e. formula (A2) where $R^3$ = isopropyl, and its salts;
(A2.5) N-[N-(4,6-dimethoxypyrimidin-2-yl)aminocarbonyl]-2-(diethylaminocarbonyl)-5-(methoxycarbonylamino)-benzenesulfonamide, i.e. formula (A2) where $R^3$ = methoxy, and its salts;
(A2.6) N-[N-(4,6-dimethoxypyrimidin-2-yl)aminocarbonyl]-2-(diethylaminocarbonyl)-5-(ethoxycarbonylamino)-benzenesulfonamide, i.e. formula (A2) where $R^3$ = ethoxy, and its salts.

Further examples of active compounds of the formula (I) are compounds of the formula (A3) and their salts

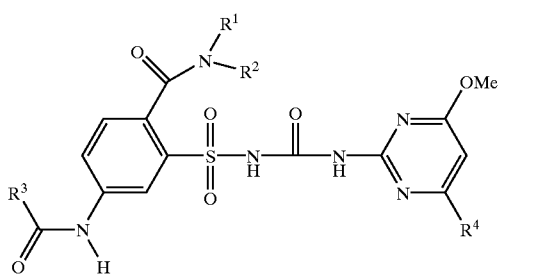

(A3)

in which $R^1$, $R^2$ and $R^3$ are as defined in formula (I) and Me=methyl and $R^4$=methoxy, chlorine or methyl, preferably compounds (A3.1) to (A3.5)

| | |
|---|---|
| (A3.1) | N-[N-(4-methoxy-6-methyl-pyrimidin-2-yl)aminocarbonyl]-2-(dimethylaminocarbonyl)-5-(formylamino)benzenesulfonamide, i.e. formula (A3) where $R^3$ = hydrogen and $R^1 = R^2$ = methyl, and its salts; |
| (A3.2) | N-[N-(4-methoxy-6-methyl-pyrimidin-2-yl)aminocarbonyl]-2-(dimethylaminocarbonyl)-5-(acetylamino)benzenesulfonamide, i.e. formula (A3) where $R^3$ = methyl and $R^1 = R^2$ = methyl, and its salts; |
| (A3.3) | N-[N-(4-methoxy-6-methyl-pyrimidin-2-yl)aminocarbonyl]-2-(dimethylaminocarbonyl)-5-(methoxycarbonyl)-benzenesulfonamide, i.e. formula (A3) where $R^3$ = methoxy and $R^1 = R^2$ = methyl, and its salts; |
| (A3.4) | N-[N-(4-methoxy-6-methylpyrimidin-2-yl)aminocarbonyl]-2-(diethylaminocarbonyl)-5-(formylamino)benzenesulfonamide, i.e. formula (A3) where $R^3$ = hydrogen and $R^1 = R^2$ = ethyl, and its salts; |
| (A3.4) | N-[N-(4-methoxy-6-methylpyrimidin-2-yl)aminocarbonyl]-2-(diethylamimocarbonyl)-5-(acetylamino)benzenesulfonamide, i.e. formula (A3) where $R^3$ = methyl and $R^1 = R^2$ = ethyl, and its salts; |
| (A3.5) | N-[N-(4-methoxy-6-methylpyrimidin-2-yl)aminocarbonyl]-2-(diethylaminocarbonyl)-5-(methoxycarbonyl)-benzenesulfonamide, i.e formula (A3) where $R^3$ = methoxy and $R^1 = R^2$ = Ethyl, and its salts. |

Said herbicides of the formula (I) and their salts inhibit the enzyme acetolactate synthase (ALS) and thus protein synthesis in plants. The application rate of the herbicides of the formula (I) can vary within a wide range, for example between 0.001 and 0.5 kg of a.s./ha (a.s./ha means here and in the following "active substance per hectare"=based on 100% active compound). In the case of applications at application rates of 0.01 to 0.1 kg of a.s./ha of the herbicides of the formula (I), preferably of the formulae (A1), (A2) or (A3), in particular (A1), pre- and postemergence a relatively broad spectrum of annual and perennial weeds, weed grasses and Cyperaceae is controlled. The application rates in the case of the combinations according to the invention are, as a rule, lower, e.g. in the range from 0.5 to 120 g of a.s./ha, preferably 2 to 80 g of a.s./ha. As a rule, the active compounds can be formulated as water-soluble powders (WP), water-dispersible granules (WDG), water-emulsifiable granules (WEG), suspoemulsions (SE) or oil suspension concentrate (SC).

For use of the active substances of the formula (I) or their salts in plant crops, it is expedient, depending on the crop, to apply a safener from certain application rates in order to reduce or to avoid damage to the crop plants. Examples of suitable safeners are those which, in combination with sulfonylurea herbicides, preferably phenylsulfonylureas, display safener action. Suitable safeners are disclosed in WO-A-96/14747 and the literature cited there.

The following groups of compounds are suitable, for example, as safeners for the abovementioned herbicidal active substances (A):

a) compounds of the dichlorophenylpyrazoline-3-carboxylic acid (S1) type, preferably compounds such as ethyl 1-(2,4-dichlorophenyl)-5-(ethoxycarbonyl)-5-methyl-2-pyrazoline-3-carboxylate (S1-1), and related compounds, such as are described in WO 91/07874.

b) derivatives of dichlorophenylpyrazolecarboxylic acid, preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4), ethyl 1-(2,4-dichlorophenyl)-5-phenylpyrazole-3-carboxylate (S1-5) and related compounds, such as are described in EP-A-333 131 and EP-A-269 806.

c) compounds of the triazolecarboxylic acids (S1) type, preferably compounds such as fenchlorazole, i.e. ethyl 1-(2,4-dichlorophenyl)-5-trichloromethyl-(1H)-1,2,4-triazole-3-carboxylate (S1-6), and related compounds (see EP-A-174 562 and EP-A-346 620);

d) compounds of the 5-benzyl- or 5-phenyl-2-isoxazoline-3-carboxylic acid, or of the 5,5-diphenyl-2-isoxazoline-3-carboxylic acid type, preferably compounds such as ethyl 5-(2,4-dichlorobenzyl)-2-isoxazoline-3-carboxylate (S1-7) or ethyl 5-phenyl-2-isoxazoline-3-carboxylate (S1-8) and related compounds, such as are described in WO 91/08202, or of ethyl 5,5-diphenyl-2-isoxazolinecarboxylate (S1-9) or n-propyl (S1-10) 5,5-diphenyl-2-isoxazolinecarboxylate or of ethyl 5-(4-fluorophenyl)-5-phenyl-2-isoxazoline-3-carboxylate (S1-11), such as are described in the German Patent Application (WO-A-95/07897).

e) compounds of the 8-quinolinoxyacetic acid (S2) type, preferably 1-methylhex-1-yl (5-chloro-8-quinolinoxy)acetate (S2-1), 1,3-dimethylbut-1-yl (5-chloro-8-quinolinoxy)acetate (S2-2), 4-allyloxybutyl (5-chloro-8-quinolinoxy)acetate (S2-3), 1-allyloxyprop-2-yl (5-chloro-8-quinol inoxy)acetate (S2-4), ethyl (5-chloro-8-quinolinoxy)acetate (S2-5), methyl (5-chloro-8-quinolinoxy)acetate (S2-6), allyl (5-chloro-8-quinolinoxy)acetate (S2-7), 2-(2-propylideneiminoxy)-1-ethyl (5-chloro-8-quinolinoxy)acetate (S2-8), 2-oxoprop-1-yl (5-chloro-8-quinolinoxy)acetate (S2-9), and related compounds such as are described in EP-A-86 750, EP-A-94 349 and EP-A-191 736 or EP-A-0 492 366.

f) compounds of the (5-chloro-8-quinoloxy)malonic acid type, preferably compounds such as diethyl (5-chloro-8-quinolinoxy)malonate, diallyl (5-chloro-8-quinolinoxy)malonate, methyl ethyl (5-chloro-8-quinolinoxy)malonate, and related compounds such as are described in EP-A-0 582 198.

g) active substances of the phenoxyacetic or propionic acid derivatives or of the aromatic carboxylic acids type, such as, for example, 2,4-dichlorophenoxyacetic acid (ester) (2,4-D), 4-chloro-2-methylphenoxypropionic acid ester (mecoprop), MCPA or 3,6-dichloro-2-methoxybenzoic acid (ester) (dicamba).

For active compounds of group (B), the abovementioned safeners are frequently also suitable. Moreover, the following safeners are suitable for the herbicide combinations according to the invention in cereal crops:

h) active substances of the pyrimidines type, which are used as soil-active safeners in rice, such as, for example,
"fenclorim" (PM, pp. 511–512) (=4,6-dichloro-2-phenylpyrimidine), which is known as a safener for pretilachlor in sown rice,
i) active substances of the pyrimidines type, which are used as soil-active safeners in rice, such as, for example,
"fenclorim" (PM, pp. 511–512) (=4,6-dichloro-2-phenylpyrimidine), which is known as a safener against damage by pretilachlor in sown rice,
j) active substances of the dichloroacetamides type, which are often used as pre-emergence safeners (soil-active safeners), such as, for example,
"dichlormid" (PM, pp. 363–364) (=N,N-diallyl-2,2-dichloroacetamide),
"R-29148" (=3-dichloroacetyl-2,2,5-trimethyl-1,3-oxazolidone from Stauffer),
"benoxacor" (PM, pp. 102–103) (=4-dichloroacetyl-3,4-dihydro-3-methyl-2H-1,4-benzoxazine).
"PPG-1292" (=N-allyl-N[(1,3-dioxolan-2-yl)methyl] dichloracetamide from PPG Industries),
"DK-24" (=N-allyl-N-[(allylaminocarbonyl)methyl] dichloracetamide from Sagro-Chem),
"AD67" or "MON 4660" (=3-dichloroacetyl-1-oxa-3-aza-spiro[4,5]decane from Nitrokemia or Monsanto),
"diclonon" or "BAS145138" or "LAB145138" (=3-dichloroacetyl-2,5,5-trimethyl-1,3-diazabicyclo[4.3.0]nonane from BASF) and
"furilazole" or "MON 13900" (see PM, 637–638) (=(RS)-3-dichloroacetyl-5-(2-furyl)-2,2-dimethyloxazolidone)
k) active substances of the dichloroacetone derivatives type, such as, for example,
"MG 191" (CAS Reg. No. 96420-72-3) (=2-dichloromethyl-2-methyl-1,3-dioxolane from Nitrokemia), which is known as a safener for corn,
l) active substances of the oxyimino compounds type, which are known as seed dressing agents, such as, for example,
"oxabetrinil" (PM, pp. 902–903) (=(Z)-1,3-dioxolan-2-ylmethoxyimino(phenyl)acetonitrile), which is known as a seed dressing safener against damage by metolachlor,
"fluxofenim" (PM, pp. 613–614) (=1-(4-chlorophenyl)-2,2,2-trifluoro-1-ethanone-O-(1,3-dioxolan-2-ylmethyl)oxime, which is known as a seed dressing safener against damage by metolachlor, and
"cyometrinil" or "CGA-43089" (PM, p. 1304) (=(Z)-cyanomethoxyimino(phenyl)acetonitrile), which is known as a seed dressing safener against damage by metolachlor,
m) active substances of the thiazolecarboxylic acid esters type, which are known as seed dressing agents, such as, for example,
"flurazole" (PM, pp. 590–591) (=benzyl 2-chloro-4-trifluoromethyl-1,3-thiazole-5-carboxylate), which is known as a seed dressing safener against damage by alachlor and metolachlor,
n) active substances of the napahthalenedicarboxylic acid derivatives type, which are known as seed dressing agents, such as, for example,
"naphthalic anhydride" (PM, p. 1342) (=1,8-naphthalenedicarboxylic anhydride), which is known as a seed dressing safener for corn against damage by thiocarbamate herbicides,
o) active substances of the chromanacetic acid derivatives type, such as, for example,
"CL 304415" (CAS Reg. No. 31541-57-8) (=2-(4-carboxychroman-4-yl)acetic acid from American Cyanamid), which is known as a safener for corn against damage by imidazolidinones,
p) active substances, which in addition to a herbicidal action against harmful plants also have safener action on crop plants such as rice, such as, for example,
"dimepiperate" or "MY-93" (PM, pp. 404–405) (=S-1-methyl-1-phenylethyl piperidine-1-thiocarboxylate), which is known as a safener for rice against damage from the herbicide molinate,
"daimuron" or "SK 23" (PM, p. 330) (=1-(1-methyl-1-phenylethyl)-3-p-tolylurea), which is known as a safener for rice against damage from the herbicide imazosulfuron,
"cumyluron"="JC-940" (=3-(2-chlorophenylmethyl)-1-(1-methyl-1-phenylethyl)urea, see JP-A60087254), which is known as a safener for rice against damage from some herbicides,
"methoxyphenone" or "NK 049" (=3,3'-dimethyl-4-methoxy-benzophenone), which is known as a safener for rice against damage from some herbicides,
"CSB" (=1-bromo-4-(chloromethylsulfonyl)benzene) (CAS Reg. No. 54091-06-4 by Kumiai), which is known as a safener against damage from some herbicides in rice.

The active substances (A) are suitable, if appropriate in the presence of safeners, for controlling harmful plants in a number of plant crops, for example in economically important crops such as cereals (e.g. wheat, barley, rye, oats, rice, corn, millet), sugarbeet, sugar cane, rapeseed, cotton and soybeans. Of particular interest here is use in cereals such as wheat and corn, in particular corn. For the combinations (A)+(B), these crops are likewise preferred. For the combinations (A)+(B3), mutant crops tolerant to the herbicides (B3) or tolerant transgenic crops are especially of particular interest, preferably corn and soybeans, in particular corn which is resistant to glufosinate or glyphosate, or soybean crops which are resistant to imidazolinones.

Suitable combinations (B) are, for example, the following compounds of the subgroups (B1) to (B3) (the herbicides are largely designated by the common name, if possible according to reference source "The Pesticide Manual" 11th Ed., British Crop Protection Council 1997, abbreviated "PM"):
(B1) foliar- and soil-acting herbicides which are effective selectively in cereal and some dicotyledonous crops against monocotyledonous and dicotyledonous harmful plants, for example
a) herbicides which are selective in corn, for example (B1.1) from the group of the acetanilides or chloracetanilides such as

---

(B1.1.1) alachlor (PM, pp. 23–24), 2-chloro-N-(2,6-diethylphenyl)-N-(methoxymethyl)acetamide,
(B1.1.2) metolachlor (PM, pp. 833–834), 2-chloro-N-(2-ethyl-6-methylphenyl)-N-(2-methoxy-1-methylethyl)acetamide,
(B1.1.3) acetochlor (PM, pp. 10–12), 2-chloro-N-(ethoxymethyl)-N-(2-ethyl-6-methylphenyl)acetamide
(B1.1.4) dimethenamid (PM, pp. 409–410), 2-chloro-N-(2,4-dimethyl-3-thienyl)-N-(2-methoxy-1-methylethyl)acetamide, -continued (B1.1.5) pethoxamid (AG Chem, New Compound Review (publ. Agranova), Vol. 17, 1999, p. 94), i.e. 2-chloro-N-(2-ethoxyethyl)-N-(2-methyl-1-phenyl-1-propenyl)acetamide,

(B1.2) from the triazines group such as (B1.2.1) atrazine (PM, pp. 55–57), N-ethyl-N'-isopropyl-6-chloro-2,4-diamino-1,3,5-triazine,
(B1.2.2) simazine (PM, pp. 1106–1108), 6-chloro-N,N-diethyl-2,4-diamino-1,3,5-triazine,
(B1.2.3) cyanazine (PM, pp. 280–283), 2-(4-chloro-6-ethylamino-1,3,5-triazin-2-ylamino)-2-methyl-propionitrile,
(B1.2.4) terbutylazine (PM, pp. 1168–1170), N-ethyl-N'-tert-butyl-6-chloro-2,4-diamino-1,3,5-triazine,
(B1.2.5) metribuzine (PM, pp. 840–841), 4-amino-6-tert-butyl-3-methylthio-1,2,4-triazin-5(4H)-one,
(B1.2.6) isoxaflutole (PM, pp. 737–739), (5-cyclopropyl-4-isoxazolyl)[2-(methylsulfonyl)-4-(trifluoromethyl)phenyl]methanone,
(B1.2.7) fluthiamid (BAY FOE 5043) (PM, pp. 82–83), 4'-fluoro-N-isopropyl-2-(5-trifluoromethyl-1,3,4-thiadiazol-2-yloxy)acetanilide,
(B1.2.8) terbutryn (PM, pp. 1170–1172), N-(1,1 dimethylethyl)-N'-ethyl-6-(methylthio)-1,3,5-triazine-2,4-diamine,

(B1.3) from the sulfonylureas group, such as (B1.3.1) nicosulfuron (PM, pp. 877–879), 2-(4,6-dimethoxypyrimidin-2-yl)-3-(3-dimethylcabamoly-2-pyridylsulfonyl)urea and its salts,
(B1.3.2) rimsulfuron (PM, pp. 1095–1097), 1-(4,6-dimethoxypyrimidin-2-yl)-3-(3-ethylsulfonyl-2-pyridylsulfonyl)urea and its salts,
(B1.3.3) primisulfuron and esters such as the methyl ester (PM, pp. 997–999), 2-[4,6-bis(difluoromethoxy)-pyrimidin-2-ylcarbamoylsulfamoyl]benzoic acid or methyl ester, and its salts,

(B1.4) from the group having different structural types, such as (B1.4.1) pendimethalin (PM, pp. 937–939), N-(1-ethylpropyl)-2,6-dinitro-3,4-xylidine,
(B1.4.2) sulcotrione (PM, pp 1124–1125), 2-(2-chloro-4-mesylbenzoyl)cyclohexane-1,3-dione,
(B1.4.3) dicamba (PM, pp. 356–357), 3,6-dichloro-o-anisic acid and its salts,
(B1.4.4) mesotrione, 2-(4-mesyl-2-nitrobenzoyl)cyclohexane-1,3-dione (ZA 1296, cf. Weed Science Society of America (WSSA) in WSSA Abstracts 1999, Vol. 39, pages 65–66, Numbers 130–132),
(B1.4.5) linuron (PM, pp. 751–753), 3-(3,4-dichlorophenyl)-1-methoxy-1-methylurea
(B1.4.6) isoxachlortole (AG Chem, New Compound Review, publ. Agranova, Vol. 16, 1998, p. 39), i.e. 4-chloro-2-(methylsulfonyl)phenyl-5-cyclopropyl-4-isoxazolyl ketone
(B1.4.7) benoxacor (PM, pp. 102–103), (±)-4-dichloroacetyl-3,4-dihydro-3-methyl-2H-1,4-benzoxazine

(B1.5) from the triazolopyrimidines group, such as (B1.5.1) metosulam (PM, pp. 836–838), 2',6'-dichloro-5,7-dimethoxy-3'-methyl[1,2,4]triazolo[1,5-a]pyrimidine-2-sulfonamide
(B1.5.2) flumetsulam (PM, pp. 573–574), 2',6'-difluoro-5-methyl[1,2,4]triazolo[1,5-a]pyrimidine-2-sulfonamide
(B1.5.3) cloransulam and esters such as the methyl ester (PM, p. 265), 3-chloro-2-(5-ethoxy-7-fluoro[1,2,4]triazolo[1,5-c]pyrimidin-2-ylsulfonamido)benzoic acid and preferably the methyl ester,
(B1.5.4) florasulam (Zeitschrift für Pflanzenkrankheiten und Pflanzenschutz, Verlag Eugen Ulmer, Stuttgart, Special Issue XVI, 1998, pp. 527–534), N-(2,6-difluorophenyl)-8-fluoro-5-methoxy(1,2,4)triazolo[1,5-C]pyrimidine-2-sulfonamide b) herbicides which are selective in rice, for example

(B1.6) from the group having different structural types, such as

| | |
|---|---|
| (B1.6.1) | molinate (PM, pp. 847–849), N-(ethylthiocarbonyl)-azepane, |
| (B1.6.2) | thiobencarb (PM, pp. 1192–1193) 4-chlorobenzyl N,N-diethylthiocarbamate |
| (B1.6.3) | quinchlorac (PM, pp. 1078–1080), 3,7-dichloroquinoline-8-carboxylic acid and its salts |
| (B1.6.4) | propanil (PM, pp. 1017–1019), N-(3,4-dichlorophenyl)propanamide |
| (B1.6.5) | pyribenzoxime, benzophenone O-[2,6-bis-[(4,6-dimethoxy-2-pyrimidinyl)oxy]benzoyl]oxime, meeting issue: The 1997 Brighton Crop Protection Conference, Weeds (publ. British Crop Protection Council) pp.39–40 |
| (B1.6.6) | butachlor (PM, pp. 159–160), N-(butoxymethyl)-2-chloro-N-(2,6-diethylphenyl)acetamide |
| (B1.6.7) | pretilachlor (PM, pp. 995–996), N-(2-propoxyethyl)-2-chloro-N-(2,6-diethylphenyl)acetamide |
| (B1.6.8) | clomazone (PM, pp. 256–257), 2-[(2-chlorophenyl)-4,4-dimethyl-3-isoxazolidinone |
| (B1.6.9) | oxadiargyl (PM, pp. 904–905), 5-tert-butyl-3-[2,4-dichloro-5-(prop-2-ynyloxy)phenyl]-1,3,4-oxadiazol-2(3H)-one |
| (B1.6.10) | oxaziclomefone, 3-[1-(3,5-dichlorophenyl)1-methylethyl]-2,3-dihydro-6-methyl-5-phenyl-4H-1,3-oxazim-4-one, meeting issue: The 1997 Brighton Crop Protection Conference, Weeds (publ. British Crop Protection Council) pp. 73–74 |
| (B1.6.11) | anilofos (PM, pp. 47–48), S-4-chloro-N-isopropylcarbaniloylmethyl-O, O-dimethylphosphorodithioate |
| (B1.6.12) | cafenstrole (PM, pp. 173–174), 1-diethylcarbamoyl-3-(2,4,6-trimethylphenylsulfonyl)-1,2,4-triazole |

-continued

| | |
|---|---|
| (B1.6.13) | mefenacet (PM, pp. 779–781), 2-(1,3-benzothiazol-3-yloxy)-N-methylacetanilide |
| (B1.6.14) | fentrazamide, 4-(2-chlorophenyl)-5-oxo-4,5-dihydrotetrazole-1-carboxylic acid cyclohexylethyl amide, meeting issue: The 1997 Brighton Crop Protection Conference, Weeds (publ. British Crop Protection Council), pp. 67–68 |
| (B1.6.15) | thiazopyr (PM, pp. 1185–1187), methyl 2-difluoromethyl-5-(4,5-dihydro-1,3-thiazol-2-yl)-4-isobutyl-6-trifluoromethylnicotinate) |
| (B1.6.16) | triclopyr (PM, pp. 1237–1239), [(3,5,6-trichloro-2-pyridinyl)oxy]acetic acid, preferably as triclopyr, triclopyr-butotyl, triclopyr-triethylammonium, |
| (B1.6.17) | oxadiazone (PM, pp. 905–907), 5-tert-butyl-3-(2,4-dichloro-5-isopropoxyphenyl)-1,3,4-oxadiazol-2(3H)-one, |
| (B1.6.18) | esprocarb (PM, pp. 472–473), S-benzyl-1,2-dimethylpropyl(ethyl)thiocarbamate |
| (B1.6.19) | pyributicarb (PM, pp. 1060–1061), O-3-tert-butylphenyl-6-methoxy-2-pyridyl-(methyl)-thiocarbamate (pyributicarb, TSH-888) |
| (B1.6.20) | azimsulfuron (PM, pp. 63–65), 1-(4,6-dimethoxypyrimidin-2-yl)-3-[1-methyl-4-(2-methyl-2H-tetrazol-5-yl)pyrazol-5-ylsulfonylurea |
| (B1.6.21) | azoles, such as are disclosed in EP-A-0663913, to which reference is hereby expressly made, e.g. 1-(3-chloro-4,5,6,7-tetrahydropyrazolo-[1,5-a]pyridin-2-yl)-5-methylpropargylamino)-4-pyrazolylcarbonitrile (in the following text "EP 913"), |
| (B1.6.22) | thenylchlor (PM, pp. 1182–1183), 2-chloro-N-(3-methoxy-2-thenyl)-2',6'-dimethylacetanilide, |
| (B1.6.23) | pentoxazone (PM, pp. 942–943), 3-(4-chloro-5-cyclopentyloxy-2-fluorophenyl)-5-isopropylidene-1,3-oxazolidine-2,4-dione, |
| (B1.6.24) | pyriminobac and its esters such as the methyl ester (PM, pp. 1071–1072), methyl 2-(4,6-dimethoxy-2-pyrimidinyloxy)-6-(1-methoxyiminoethyl)benzoate, also as the acid or sodium salt, |
| (B1.6.25) | OK 9701 (AG Chem, New Compound Review, publ. Agranova, Vol. 17, 1999, p. 75), |
| (B1.6.26) | quizalofop/quizalofop-P and its esters such as the ethyl or tefuryl ester (PM, pp. 1087–1092), (RS)-2-[4-(6-chloroquinoxalin-2-yloxy)phenoxy]propionic acid |
| (B1.6.27) | fenoxaprop/fenoxaprop-P or its esters such as the ethyl ester (PM, pp. 519–520), ethyl 2-[4-(6-chlorobenzoxazol-2-yloxy)phenoxy]propionate |
| (B1.6.28) | fluazifop/fluazifop-P and its esters such as the butyl ester (PM, pp. 553–557), butyl (RS)-2-[4-(5-trifluoromethyl-2-pyridyloxy)phenoxy]propionate |
| (B1.6.29) | haloxyfop/haloxyfop-P and its esters such as the methyl ester (PM, pp. 659–663), (±)-2-[4-[[3-chloro-5-(trifluoromethyl)-2-pyridinyl]oxy]phenoxy]propionic acid, including, inter alia, the application form as haloxyfop-etotyl, haloxyfop-methyl, haloxyfop-methyl [(R)-isomer] |
| (B1.6.30) | propaquizafop (PM, pp. 1021–1022), 2-isopropylidenaminooxyethyl (R)-2-[4-(6-chloroquinoxalin-2-yloxy)phenoxy]propionate |
| (B1.6.31) | clodinafop and its esters such as the propargyl ester (PM, pp. 251–253), (R)-2-[4-(5-chloro-3-fluoro-2-pyridyloxy)phenoxy]propionic acid |
| (B1.6.32) | cyhalofop and its esters such as the butyl ester (PM, pp. 297–298), butyl (R)-2-[4-(4-cyano-2-fluorophenoxy)phenoxy]propionate |
| (B1.6.33) | sethoxydim (PM, pp. 1101–1103), (±)-(EZ)-(1-ethoxyiminobutyl)-5-[2-ethylthio)propyl]-3-hydroxycyclohex-2-enone |
| (B1.6.34) | cycloxydim (PM, pp. 290–291), (±)-2-[1-(ethoxyimino)butyl]-3-hydroxy-5-thian-3-ylcyclohex-2-enone |
| (B1.6.35) | clethodim (PM, pp. 250–251), (±)-2-[(E)-1-[(E)-3-chloroallyloxyimino]propyl]-5-[2-(ethylthio)propyl]-3-hydrocyclohex-2-enone |
| (B1.6.36) | clefoxidim, 2-[1-(2-(4-chlorophenoxy)propoxyimino)butyl]-3-oxo-5-thione-3-ylcyclohex-1-enol (AG Chem, New Compound Review (publ. Agranova), Vol. 17, 1999, pp. 26) | c) herbicides which are selective in wheat, rye, oats or barley, for example
 (B1.7) from the group having different structural types, such as

| | |
|---|---|
| (B1.7.1) | isoproturon (PM, pp. 732–734), 3-(4-isopropylphenyl)-1,1-dimethylurea |
| (B1.7.2) | chlortoluron (PM, pp. 229–231), 3-(3-chloro-p-tolyl)-1,1-dimethylurea |
| (B1.7.3) | prosulfocarb (PM, pp. 1039–1041), S-benzyl dipropylthiocarbamate |
| (B1.7.4) | MON 48500, isopropyl 5-[4-bromo-1-methyl-5-(trifluoromethyl)-1H-pyrazol-3-yl]-2-chloro-4-fluorobenzoate, (meeting issue: The 1997 Brighton Crop Protection Conference, Weeds (publ. British Crop Protection Council), pp. 45–46) |
| (B1.7.5) | diclofop/diclofop-P and its esters such as the methyl ester (PM, pp. 374–377), (RS)-2-(2,4-dichlorophenoxy)phenoxy]propionic acid |
| (B1.7.6) | imazamethabenz (PM, pp. 694–696), methyl (±)-6-(4-isopropyl-4-methyl-5-oxo-2-imidazolin-2-yl)-m-toluate and methyl (±)-2-(4-isopropyl-4-methyl-5-oxo-2-imidazolin-2-yl)-p-toluate |
| (B1.7.7) | triasulfuron and its salts (PM, pp. 1222–1224), 1-[2-(2-chloroethoxy)phenylsulfonyl]-3-(4-methoxy-6-methyl-1,3,5-triazin-2-yl)urea |
| (B1.7.8) | flupyrsulfuron and its esters such as the methyl ester and its salts (PM, pp. 586–588), methyl 2-(4,6-dimethoxypyrimidin-2-ylcarbamoylsulfamoyl)-6-trifluoromethylnicotinate sodium) |
| (B1.7.9) | sulfonylureas such as are disclosed in US 5,648,315, to which reference is hereby expressly made, e.g. N-[(4,6-dimethoxypyrimidin-2-yl)aminocarbonyl]-5-methylsulfonamidoethyl-2-methoxycarbonylbenzolsulfonamide (in the following text "US 315") |

(B2) herbicides which are effective selectively in cereals and some dicotyledonous crops against predominantly dicotyledonous harmful plants, for example
 a) herbicides which are selective in corn, for example
 (B2.1) from the growth hormones group of the auxin type, such as

| | |
|---|---|
| (B2.1.1) | MCPA (PM, pp. 767–769), (4-chloro-2-methylphenoxy)acetic acid and its salts and esters, |
| (B2.1.2) | 2,4-D (PM, pp. 323–327), 2,4-dichlorophenoxyacetic acid and its salts and esters, |

(B2.2) from the hydroxybenzonitriles (HBN) group, such as

| | |
|---|---|
| (B2.2.1) | bromoxynil (PM, pp., 149–151), 3,5-dibromo-4-hydroxybenzontrile, |

(B2.3) from the group having different structural types, such as

| | |
|---|---|
| (B2.3.1) | bentazone (PM, pp. 1064–1066), 3-isopropyl-2,2-dioxo-1H-2,1,3-benzothiadiazine-4(3H)-one, |
| (B2.3.2) | fluthiacet (PM, pp. 606–608), [2-chloro-4-fluoro-5-(5,6,7,8-tetrahydro-3-oxo-1H, 3H-1,3,4-thiadiazolo(3,4-a]pyridazin-1-ylidenamino)phenylthio]acetic acid and preferably the methyl ester, |
| (B2.3.3) | pyridate (PM, pp. 1064–1066), O-(6-chloro-3-phenylpyridazin-4-yl) S-octyl thiocarbonate, |
| (B2.3.4) | diflufenzopyr (BAS 654 00 H, PM pp. 81–82), 2-{1-[4-(3,5-difluorophenyl)semicarbazono]ethyl}nicotinic acid |
| (B2.3.5) | carfentrazone (PM, pp. 191–193), ethyl (RS)-2-chloro-3-[2-chloro-5-(4-difluoromethyl-4,5-dihydro-3-methyl-5-oxo-1H-1,2,4-triazol-1-yl)-4-fluorophenyl]propionate used, inter alia, as carfentrazone-ethyl (as indicated) or alternatively as the acid |
| (B2.3.6) | clopyralid (PM, pp. 260–263), 3,6-dichloropyridine-2-carboxylic acid |

(B2.4) from the sulfonylureas group, such as

| | |
|---|---|
| (B2.4.1) | halosulfuron (PM, pp. 657–659), 3-chloro-5-(4,6-dimethoxypyrimidin-2-ylcarbamoylsulfamoyl)-1-methylpyrazole-4-carboxylic acid and its esters and salts, preferably the methyl ester, |
| (B2.4.2) | thifensulfuron and its esters, preferably the methyl ester (PM, pp. 1188–1190), 3-[[[[(4-methoxy-6-methyl-1,3,5-triazin-2-yl)amino]carbonyl]amino]sulfonyl]-2-thiophenecarboxylic acid or methyl ester and its salts, |
| (B2.4.3) | prosulfuron and its salts (PM, pp. 1041–1043), 1-(4-methoxy-6-methyl-1,3,5-triazin-2-yl)-3-[2-(3,3,3-trifluoropropyl)phenylsulfonyl]urea and its salts, |
| (B2.4.4) | iodosulfuron (proposed common name) and preferably esters such as the methyl ester and their salts (cf. WO 96/41537 to which reference is hereby expressly made), 4-iodo-2-(4-methoxy-6-methyl-1,3,5-triazin-2-ylcarbamoylsulfamoyl)benzoic acid or methyl ester and its salts such as the sodium salt, disclosed in WO-A-92/13845, to which reference is hereby expressly made, |
| (B2.4.5) | tritosulfuron and its salts (AG Chem, New Compound Review (publ. Agranova), Vol. 17, 1999, pp. 24), N-[[[4'-methoxy(trifluoromethyl)-1,3,5-triazin-2-yl]amino]carbonyl]-2-trifluoromethylbenzenesulfonamide) |
| (B2.4.6) | sulfosulfuron and its salts (PM, pp. 1130–1131), 1-(4,6-dimethoxypyrimidin-2-yl)-3-(2-ethylsulfonylimidazo[1,2-a]pyridin-3-yl)sulfonylurea | b) herbicides which are selective in rice, for example
 (B2.5) from the group having different structural types, such as

| | |
|---|---|
| (B2.5.1) | 2,4-D (PM, pp. 323–327), (2,4-dichlorophenoxy)acetic acid, frequently employed forms: 2,4-D-butotyl, 2,4-D-butyl, 2,4-D-dimethylammonium, 2,4-D-diolamine, 2,4-D-isooctyl, 2,4-D-isopropyl, 2,4-D-trolamine |
| (B2.5.2) | MCPA (PM, pp. 770–771), (4-chloro-2-methylphenoxy)acetic acid, predominantly employed forms are, inter alia, MCPA-butotyl, MCPA-dimethylammonium, MCPA-isoctyl, MCPA-potassium, MCPA-sodium |
| (B2.5.3) | bensulfuron and its esters, preferably the methyl ester and its salts, (PM, pp. 104–105), methyl α-(4,6-dimethoxypyrimidin-2-ylcarbamoylsulfamoyl)-O-toluate |

-continued

| | |
|---|---|
| (B2.5.4) | methsulfuron and its esters, preferably the methyl ester, and their salts (PM, pp. 842–844), methyl 2-[[[[(4-methoxy-6-methyl-1,3,5-triazin-2-yl)amino]carbonyl]amino]sulfonyl]benzoate |
| (B2.5.6) | acifluorfen (PM, pp. 12–14), 5-(2-chloro-α,α,α,-trifluoro-p-tolyloxy)-2-nitrobenzoic acid also used as acifluorfen-sodium |
| (B2.5.7) | bispyribac (KIH 2023), the form as a sodium salt is preferred (PM, pp. 129–131), sodium 2,6-bis[(4,6-dimethoxypyrimidin-2-yl)oxy]benzoate |
| (B2.5.8) | ethoxysulfuron and its esters and salts (PM, pp. 488–490), 1-(4,6-dimethoxypyrimidin-2-yl)-3-(2-ethoxyphenoxysulfonyl)urea |
| (B2.5.9) | cinosulfuron and its esters and salts (PM, pp. 248–250), 1-(4,6-dimethoxy-1,3,5-triazin-2-yl)-3-[2-(2-methoxyethoxy)phenylsulfonyl]urea |
| (B2.5.10) | pyrazosulfuron and its esters, preferably the ethyl ester, and their salts (PM, pp. 1052–1054), methyl 5-(4,6-dimethoxypyrimidin-2-ylcarbamoylsulfamoyl)-1-methylpyrazole-4-carboxylate |
| (B2.5.11) | imazosulfuron and its esters and salts (PM, pp. 703–704), 1-(2-chloroimidazo[1,2-a]pyridin-3-ylsulfonyl)-3-(4,6-dimethoxypyrimidin-2-yl]urea |
| (B2.5.12) | cyclosulfamuron and its esters and salts (PM, pp. 288–289), N-[[[2-(cyclopropylcarbonyl)phenyl]amino]sulfonyl]-N1-(4,6-dimethoxypyrimidin-2-yl)urea |
| (B2.5.13) | chlorsulfuron and its esters and salts (PM, pp. 239–240), 1-(2-chlorophenylsulfonyl)-3-(4-methoxy-6-methyl-1,3,5-triazin-2-yl)urea |
| (B2.5.14) | bromobutide (PM, pp. 144–145), 2-bromo-3,3-dimethyl-N-(1-methyl-1-phenylethyl)butyramide |
| (B2.5.15) | bentazone (PM, pp. 109–111), 3-isopropyl-1H-2,1,3-benzothiadiazin-4(3H)-one-2,2-dioxide |
| (B2.5.16) | benfuresate (PM, pp. 98–99), 2,3-dihydro-3,3-dimethylbenzofuran-5-ylethanesulfonate |
| (B2.5.17) | chlorimuron and its esters, preferably the ethyl ester, and their salts (PM, pp. 217–218), ethyl 2-(4-chloro-6-methoxypyrimidin-2-ylcarbonylsulfamoyl)benzoate | c) herbicides which are selective in wheat, rye, oats or barley, for example (B2.6) from the group having different structural types, such as

| | |
|---|---|
| (B2.6.1) | diflufenican (PM, pp. 397–399), 2',4'-difluoro-2-(α,α,α-trifluoro-m-tolyloxy)nicotinanilide |
| (B2.6.2) | flurtamone (PM, pp. 602–603), (RS)-5-methylamino-2-phenyl-4-(α,α,α-trifluoro-m-tolyl)furan-3(2H)one |
| (B2.6.3) | tribenuron (PM, pp. 1230–1232), methyl 2-[[[[-methoxy-6-methyl-1,3,5-triazin-2-yl)methylamino]carbonyl]amino]sulfony]benzoate |
| (B2.6.4) | amidosulfuron and its salts (PM, pp. 37–38), 1-(4,6-dimethoxypyrimidin-2-yl)-3-mesyl(methyl)sulfamoylurea |
| (B2.6.5) | mecoprop/mecoprop-p and their esters (PM, pp. 776–779), (RS)-2-(4-chloro-o-tolyloxy)propionic acid |
| (B2.6.6) | dichlorprop/dichlorprop-P and their esters (PM, pp. 368–372), (RS)-2-(2,4-dichlorophenoxy)propionic acid |
| (B2.6.7) | fluroxypyr (PM, pp. 597–600), 4-amino-3,5-dichloro-6-fluoro-2-pyridyloxyacetic acid |
| (B2.6.8) | picloram (PM, pp. 977–979), 4-amino-3,5,6-trichloropyridine-2-carboxylic acid |
| (B2.6.9) | ioxynil (PM, pp. 718–721), 4-hydroxy-3,5-di-iodobenzonitrile |
| (B2.6.10) | bifenox (PM, pp. 116–117), methyl-5-(2,4-dichlorophenoxy)-2-nitrobenzoate |
| (B2.6.11) | pyraflufenethyl (PM, pp. 1048–1049), ethyl 2-chloro-5-(4-chloro-5-difluoromethoxy-1-methylpyrazol-3-yl)-4-fluorophenoxyacetate |
| (B2.6.12) | fluoroglycofenethyl (PM, pp. 580–582), O-[5-(2-chloro-α,α,α-trifluoro-p-tolyloxy)-2-nitrobenzoyl]glycolic acid |
| (B2.6.13) | cinidonethyl (BAS 615005) (AG Chem, New Compound Review, publ. Agranova, Vol. 17, 1999, p. 26) |
| (B2.6.14) | picolinofen (AG Chem, New Compound Review, (publ. Agranova), Vol. 17, 1999, pp. 35), N-4-fluorophenyl-6-(3-trifluoromethylphenoxy)pyridine-2-carboxamide |

(B3) herbicides which are effective against monocotyledonous and dicotyledonous harmful plants for use in a nonselective area or in specifically tolerant crops, such as (B3.1) glufosinate (PM, pp. 643–645), D,L-2-amino-4-[hydroxy(methyl)phosphinyl]butanoic acid and its salts and esters, for example

| | |
|---|---|
| (B3.1.1) | glufosinate-ammonium, the monoammonium salt of the acid form, |

(B3.2) glyphosate (PM, pp. 646–649), N-(phosphonomethyl)glycine and its salts and esters, for example

| | |
|---|---|
| (B3.2.1) | glyphosate-isopropylammonium |

(B3.3) imidazolinones and their salts such as

| | |
|---|---|
| (B3.3.1) | imazapyr and its salts and esters (PM, pp. 697–699), |
| (B3.3.2) | imazethapyr and its salts and esters (PM, pp. 701–703), |
| (B3.3.3) | imazamethabenz and its salts and esters (PM, pp. 694–696), |
| (B3.3.4) | imazamethabenz-methyl (PM, pp. 694–696), |
| (B3.3.5) | imazamox and its salts and esters (PM, pp. 696–697), |
| (B3.3.6) | imazaquin and its salts and esters, e.g. the ammonium salt (PM, pp. 699–701) and |
| (B3.3.7) | imazapic (AC 263,222) and its salts and esters, e.g. the ammonium salt, (PM, pp. 5 and 6, reported under AC 263,222). |

When the short form of the common name is used, all customary derivatives are included thereby, such as the esters and salts, and isomers, in particular optical isomers, in particular the commercially available form or forms. The chemical compound names indicated designate at least one of the compounds included by the common name, frequently a preferred compound. In the case of sulfonylureas, the term salts also includes those which are formed by replacement of a hydrogen atom on the sulfonamide group by a cation.

Preferred herbicide combinations are those of one or more compounds (A) with one or more compounds of the group (B1) or (B2) or (B3).

Further preferred combinations are those of compounds (A) with one or more compounds (B) according to the scheme:

(A)+(B1)+(B2), (A)+(B1)+(B3), (A)+(B2)+(B3) or (A)+(B1)+(B2)+(B3)

Those combinations are also novel here to which one or more further active substances of different structure [active substances (C)] are additionally added, such as (A)+(B1)+(C), (A)+(B2)+(C) or (A)+(B3)+(C), (A)+(B1)+(B2)+(C), (A)+(B1)+(B3)+(C), (A)+(B2)+(B3)+(C)

or (A)+(B1)+(B2)+(B3)+(C).

For combinations of the last-mentioned type with three or more active substances, the preferred conditions explained below, in particular for two-substance combinations according to the invention, likewise primarily apply if the two-substance combinations according to the invention are contained therein and with respect to the two-substance combination concerned.

The application rates of the herbicides (B) can vary strongly from herbicide to herbicide. As a rule of thumb, for preferred application rates for some mixture components of group (B), the following details [in g of a.s. (active substance)/ha (hectare)] can apply, it also being possible in the combinations according to the invention for amounts below the lowest amount to be useful:

for compounds (B1.1.1), (B1.1.2), (B1.1.3), (B1.1.4), (B1.2.1), (B1.2.2), (B1.2.3), (B1.2.4), (B1.2.5):
  100–4000, preferably 500–4000, g of A.S./ha pre- and post-emergence against weeds and especially weed grasses, for compounds (B1.2.6):
  10–200, preferably 75–150, g of A.S./ha pre- and post-emergence against weeds and weed grasses, for compounds (B1.2.7):
  10 (in particular 100)–500, preferably 100–600, g of A.S./ha pre- and post-emergence against weeds and weed grasses, for compounds (B1.3):
  1–60, preferably 5–60, g of A.S./ha pre- and post-emergence against weeds and weed grasses; usually foliar action, in some cases soil action, for compounds (B1.4):
  10 (in particular 25)–2500, preferably 50–2500, g of A.S./ha against weeds and weed grasses post-emergence, but also pre-emergence, for compounds (B2.1):
    10 (in particular 100)–3000 g of A. S./ha predominantly against weeds and Cyperaceae post-emergence, for compounds (B2.2):
  10 (in particular 50)–1000 g of A.S./ha predominantly against weeds post-emergence, for compounds (B2.3.1):
  50 (in particular 500)–2500 g of A.S./ha predominantly against weeds post-emergence, for compounds (B2.3.2):
  50 (in particular 300)–1500 g of A.S./ha predominantly against weeds post-emergence, for compounds (B2.3.3):
  100 (in particular 150)–1500 g of A.S./ha predominantly against weeds post-emergence, for compounds (B2.4):
  0.5–180, preferably 5–80, g of A.S./ha predominantly against weeds post-emergence, for compounds (B3.1) and (B3.2):
  20 (in particular 100)–2000 g of A.S./ha in plantation crops and in uncultivated land for controlling weed grasses and weeds post-emergence; moreover in tolerant, transgenic crops for controlling weed grasses and weeds post-emergence;

for compounds (B3.3):
  10–500, preferably 100–200, g of A.S./ha in plantation crops and in uncultivated land for controlling weed grasses and weeds pre- and post-emergence; moreover in tolerant, mutant/transgenic crops for controlling weed grasses and weeds pre- and post-emergence.

Ranges of suitable quantitative ratios of the compounds (A) and (B) follow from the application rates mentioned for the individual substances. In the combinations according to the invention, as a rule, the application rates can be reduced.

Preferred quantitative ranges (in g of A.S./ha)/mixing ratios (A):(B), preferably (A1):(B), for the combinations according to the invention are listed below:

| | |
|---|---|
| (A) + (B1.1.1), (B1.1.2), (B1.1.3), (B1.1.4), (B1.1.5), (B1.2.1), (B1.2.2), (B1.2.3), (B1.2.4) or (B1.2.5): | 10–100 + 100–3000/1:1 to 1:300, preferably 1:20 to 1:80 |
| (A) + (B1.2.6): | 10–100 + 10–200 (in particular 10–100)/10:1 to 1:20 (in particular 1:10), preferably 5:1 to 1:5, |
| (A) + (B1.2.7): | 10–100 + 10–1500 (in particular 10–400)/10:1 to 1:150 (in particular 1:40), preferably 5:1 to 1:40 (in particular 1:20), |
| (A) + (B1.2.8): | 10–100 + 250–3000 (in particular 500–2000)/1:300 to 1:3, preferably 1:100 to 1:7 |
| (A) + (B1.3): | 10–100 + 1–60 (in particular 1–50)/100:1 to 1:6 (in particular 1:5), preferably 50:1 to 1:2, |
| (A) + (B1.4): | 10–100 + 10–2500 (in particular 10–1000)/10:1 to 1:250 (in particular 1:10), preferably 1:1 to 1:75 (in particular 1:5), |
| (A) + (B1.5.1), (B1.5.2) or (B1.5.3): | 10–100 + 5–200 (in particular 10–150)/1:20 to 20:1, preferably 1:8 to 6:1 |
| (A) + (B1.5.4): | 10–100 + 1–15 (in particular 3–12)/1:3 to 90:1, preferably 1:1 to 20:1 |
| (A) + (B1.6.1)–(B1.6.25): | 10–100 + 0.5 –5000 (in particular 1–4000)/200:1 to 1:500, preferably 120:1 to 1:200 |
| (A) + (B1.6.26)–(B1.6.32): | 10–100 + 5–500 (in particular 10–400)/20:1 to 1:50, preferably 6:1 to 1:20 |
| (A) + (B1.6.33)–(B1.6.36): | 10–100 + 10–1000 (in particular 25–800)/10:1 to 1:100, preferably 2.5:1 to 1:40 |
| (A) + (B1.7.1)–(B1.7.6): | 10–100 + 5–5000 (in particular 10–4000)/20:1 to 1:500, preferably 6:1 to 1:200 |
| (A) + (B1.7.7), (B1.7.8) or (B1.7.9): | 10–100 + 1–80 (in particular 2–60)/100:1 to 1:8, preferably 30:1 to 1:3 |

-continued

| | |
|---|---|
| (A) + (B2.1): | 10–100 + 10–3000 (in particular 10–2500)/10:1 (in particular 1:1) to 1:300 (in particular 1:250), preferably 3:1 to 1:100 |
| (A) + (B2.2): | 10–100 + 10–1000 (in particular 10–800)/10:1 (in particular 2:1) to 1:80 (in particular 1:10) |
| (A) + (B2.3.1): | 10–100 + 50–2500 (in particular 50–2000)/2:1 (in particular 1:5) to 1:250 (in particular 1:200), preferably 1:1 (in particular 1:13) to 1:100 (in particular 1:33), |
| (A) + (B2.3.2): | 10–100 + 50–1000/2:1 to 1:100, preferably 1:1 to 1:50, |
| (A) + (B2.3.3): | 10–100 + 100 (in particular 150)–1500, (in particular 300–1200)/1:1 to 1:150, preferably in particular 1:3 to 1:60, |
| (A) + (B2.3.4): | 10–100 + 20–300 (in particular 40–200)/1:60 to 5:1, preferably 1:20–1.5:1 |
| (A) + (B2.3.5): | 10–100 + 5–120 (in particular 10–90)/20:1 to 1:12, preferably 6:1 to 1:4 |
| (A) + (B2.3.6): | 10–100 + 25–500 (in particular 50–300)/4:1 to 1:50, preferably 2:1 to 1:30, |
| (A) + (B2.4): | 10–100 + 0.5–180 (in particular 1–80)/200:1 (in particular 100:1) to 1:18 (in particular 1:8), preferably 60:1 (in particular 50:1) to 1:7 (in particular 1:5), |
| (A) + (B2.5): | 10–100 + 0.5–2000 (in particular 1–1500)/200:1 to 1:200, preferably 60:1 to 1:75 |
| (A) + (B2.6.1) or (B2.6.2): | 10–100 + 2.5–400 (in particular 5–200)/40:1 to 1:40, preferably 12:1 to 1:10 |
| (A) + (B2.6.3) or (B2.6.4): | 10–100 + 2.5–80 (in particular 5–60)/40:1 to 1:8, preferably 12:1 to 1:3 |
| (A) + (B2.6.5)– (B2.6.8): | 10–100 + 50–2000 (in particular 60–1800)/2:1 to 1:200, preferably 1:2 to 1:90 |
| (A) + (B2.6.9) or (B2.6.10): | 10–100 + 50–3000 (in particular 80–2000)/2:1 to 1:300, preferably 1:4 to 1:100 |
| (A) + (B2.6.11), (B2.6.12) or (B2.6.13): | 10–100 + 15–180 (in particular 2.5–150)/60:1 to 1:18, preferably 30:1 to 1:7 |
| (A) + (B6.1.14): | 10–100 + 2.5–80 (in particular 5–60)/40:1 to 1:8, preferably 12:1 to 1:3 |
| (A) + (B3.1): | 10–100 + 100–2000 (in particular 20–1600)/5:1 (in particular 1:1) to 1:200 (in particular 1:160), preferably 3:1 (in particular 1:3) to 1:90 (in particular 1:80) |
| (A) + (B3.2): | 10–100 + 20–2000 (in particular 20–1600)/5:1 (in particular 1:1) to 1:200 (in particular 1:160), preferably 3:1 (in particular 1:3) to 1:90 (in particular 1:80) |
| (A) + (B3.3): | 10–100 + 10–500 (in particular 20–150)/20:1 (in particular 5:1) to 1:50 (in particular 1:20), preferably 4:1 (in particular 3:1) to 1:10. |

Of particular interest is the use of herbicidal agents containing the following compounds (A)+(B):

(A1.1)+(B1.1.1), (A1.1)+(B1.1.2), (A1.1)+(B1.1.3), (A1.1)+(B1.1.4), (A1.1)+(B1.1.5), (A1.1)+(B1.2.1), (A1.1)+(B1.2.2), (A1.1)+(B1.2.3), (A1.1)+(B1.2.4), (A1.1)+(B1.2.5), (A1.1)+(B1.2.6), (A1.1)+(B1.2.7), (A1.1)+(B1.2.8), (A1.1)+(B1.3.1), (A1.1)+(B1.3.2), (A1.1)+(B1.3.3), (A1.1)+(B1.4.1), (A1.1)+(B1.4.2), (A1.1)+(B1.4.3), (A1.1)+(B1.4.4), (A1.1)+(B1.4.5), (A1.1)+(B1.4.6), (A1.1)+(B1.4.7), (A1.1)+(B1.5.1), (A1.1)+(B1.5.2), (A1.1)+(B1.5.3), (A1.1)+(B1.5.4), (A1.1)+(B1.6.1), (A1.1)+(B1.6.2), (A1.1)+(B1.6.3), (A1.1)+(B1.6.4), (A1.1)+(B1.6.5), (A1.1)+(B1.6.6), (A1.1)+(B1.6.7), (A1.1)+(B1.6.8), (A1.1)+(B1.6.9), (A1.1)+(B1.6.10), (A1.1)+(B1.6.11), (A1.1)+(B1.6.12), (A1.1)+(B1.6.13), (A1.1)+(B1.6.14), (A1.1)+(B1.6.15), (A1.1)+(B1.6.16), (A1.1)+(B1.6.17), (A1.1)+(B1.6.18), (A1.1)+(B1.6.19), (A1.1)+(B1.6.20), (A1.1)+(B1.6.21), (A1.1)+(B1.6.22), (A1.1)+(B1.6.23), (A1.1)+(B1.6.24), (A1.1)+(B1.6.25), (A1.1)+(B1.6.26), (A1.1)+(B1.6.27), (A1.1)+(B1.6.28), (A1.1)+(B1.6.29), (A1.1)+(B1.6.30), (A1.1)+(B1.6.31), (A1.1)+(B1.6.32), (A1.1)+(B1.6.33), (A1.1)+(B1.6.34), (A1.1)+(B1.6.35), (A1.1)+(B1.6.36), (A1.1)+(B1.7.1), (A1.1)+(B1.7.2), (A1.1)+(B1.7.3), (A1.1)+(B1.7.4), (A1.1)+(B1.7.5), (A1.1)+(B1.7.6), (A1.1)+(B1.7.7), (A1.1)+(B1.7.8), (A1.1)+(B1.7.9), (A1.1)+(B2.1.1), (A1.1)+(B2.1.2), (A1.1)+(B2.2.1), (A1.1)+(B2.3.1), (A1.1)+(B2.3.2), (A1.1)+(B2.3.3), (B2.3.4), (A1.1)+(B2.3.5), (A1.1)+(B2.3.6), (A1.1)+(B2.4.1), (A1.1)+(B2.4.2), (A1.1)+(B2.4.3), (A1.1)+(B2.4.4), (A1.1)+(B2.4.5), (A1.1)+(B2.4.6), (A1.1)+(B2.5.1), (A1.1)+(B2.5.2), (A1.1)+(B2.5.3), (A1.1)+(B2.5.4), (A1.1)+(B2.5.5), (A1.1)+(B2.5.6), (A1.1)+(B2.5.7), (A1.1)+(B2.5.8), (A1.1)+(B2.5.9), (A1.1)+(B2.5.10), (A1.1)+(B2.5.11), (A1.1)+(B2.5.12), (A1.1)+(B2.5.13), (A1.1)+(B2.5.14), (A1.1)+(B2.5.16), (A1.1)+(B2.5.17), (A1.1)+(B2.6.1), (A1.1)+(B2.6.2), (A1.1)+(B2.6.3), (A1.1)+(B2.6.4), (A1.1)+(B2.6.5), (A1.1)+(B2.6.6), (A1.1)+(B2.6.7), (A1.1)+(B2.6.8), (A1.1)+(B2.6.9), (A1.1)+(B2.6.10), (A1.1)+(B2.6.11), (A1.1)+(B2.6.12), (A1.1)+(B2.6.13), (A1.1)+(B2.6.14), (A1.1)+(B3.1.1), (A1.1)+(B3.2.1), (A1.1)+(B3.3.1), (A1.1)+(B3.3.2), (A1.1)+(B3.3.3), (A1.1)+(B3.3.4), (A1.1)+(B3.3.5), (A1.1)+(B3.3.6) and (A1.1)+(B3.3.7), (A1.2)+(B1.1.1), (A1.2)+(B1.1.2), (A1.2)+(B1.1.3), (A1.2)+(B1.1.4), (A1.2)+(B1.1.5), (A1.2)+(B1.2.1), (A1.2)+(B1.2.2), (A1.2)+(B1.2.3), (A1.2)+(B1.2.4), (A1.2)+(B1.2.5), (A1.2)+(B1.2.6), (A1.2)+(B1.2.7), (A1.2)+(B1.2.8), (A1.2)+(B1.3.1), (A1.2)+(B1.3.2), (A1.2)+(B1.3.3), (A1.2)+(B1.4.1), (A1.2)+(B1.4.2), (A1.2)+(B1.4.3), (A1.2)+(B1.4.4), (A1.2)+(B1.4.5), (A1.2)+(B1.4.6), (A1.2)+(B1.4.7), (A1.2)+(B1.5.1), (A1.2)+(B1.5.2), (A1.2)+(B1.5.3), (A1.2)+(B1.5.4), (A1.2)+(B1.6.1), (A1.2)+(B1.6.2), (A1.2)+(B1.6.3), (A1.2)+(B1.6.4), (A1.2)+(B1.6.5), (A1.2)+(B1.6.6), (A1.2)+(B1.6.7), (A1.2)+(B1.6.8), (A1.2)+(B1.6.9), (A1.2)+(B1.6.10), (A1.2)+(B1.6.11), (A1.2)+(B1.6.12), (A1.2)+(B1.6.13), (A1.2)+(B1.6.14), (A1.2)+(B1.6.15), (A1.2)+(B1.6.16), (A1.2)+(B1.6.17), (A1.2)+(B1.6.18), (A1.2)+(B1.6.19), (A1.2)+(B1.6.20), (A1.2)+(B1.6.21), (A1.2)+(B1.6.22), (A1.2)+(B1.6.23), (A1.2)+(B1.6.24), (A1.2)+(B1.6.25), (A1.2)+(B1.6.26), (A1.2)+(B1.6.27), (A1.2)+(B1.6.28), (A1.2)+(B1.6.29), (A1.2)+(B1.6.30), (A1.2)+(B1.6.31), (A1.2)+(B1.6.32), (A1.2)+(B1.6.33), (A1.2)+(B1.6.34), (A1.2)+(B1.6.35), (A1.2)+(B1.6.36), (A1.2)+(B1.7.1), (A1.2)+(B1.7.2), (A1.2)+(B1.7.3), (A1.2)+(B1.7.4), (A1.2)+(B1.7.5), (A1.2)+(B1.7.6), (A1.2)+(B1.7.7), (A1.2)+(B1.7.8), (A1.2)+(B1.7.9), (A1.2)+(B2.1.1), (A1.2)+(B2.1.2), (A1.2)+(B2.2.1), (A1.2)+(B2.3.1), (A1.2)+(B2.3.2), (A1.2)+(B2.3.3), (A1.2)+(B2.3.4), (A1.2)+(B2.3.5), (A1.2)+(B2.3.6), (A1.2)+(B2.4.1), (A1.2)+(B2.4.2), (A1.2)+(B2.4.3), (A1.2)+(B2.4.4), (A1.2)+(B2.4.5), (A1.2)+(B2.4.6), (A1.2)+(B2.5.1), (A1.2)+(B2.5.2), (A1.2)+(B2.5.3), (A1.2)+(B2.5.4), (A1.2)+(B2.5.5), (A1.2)+(B2.5.6), (A1.2)+(B2.5.7), (A1.2)+(B2.5.8), (A1.2)+(B2.5.9), (A1.2)+(B2.5.10), (A1.2)+(B2.5.11), (A1.2)+(B2.5.12), (A1.2)+(B2.5.13), (A1.2)+(B2.5.14), (A1.2)+(B2.5.16), (A1.2)+(B2.5.17), (A1.2)+(B2.6.1), (A1.2)+(B2.6.2), (A1.2)+(B2.6.3), (A1.2)+(B2.6.4), (A1.2)+(B2.6.5), (A1.2)+(B2.6.6), (A1.2)+(B2.6.7), (A1.2)+(B2.6.8), (A1.2)+(B2.6.9), (A1.2)+(B2.6.10), (A1.2)+(B2.6.11), (A1.2)+(B2.6.12), (A1.2)+(B2.6.13), (A1.2)+(B2.6.14), (A1.2)+(B3.1.1), (A1.2)+(B3.2.1), (A1.2)+(B3.3.1), (A1.2)+(B3.3.2), (A1.2)+(B3.3.3), (A1.2)+(B3.3.4), (A1.2)+(B3.3.5), (A1.2)+(B3.3.6) and (A1.2)+(B3.3.7), (A1.5)+(B1.1.1), (A1.5)+(B1.1.2), (A1.5)+(B1.1.3), (A1.5)+(B1.1.4), (A1.5)+(B1.1.5), (A1.5)+(B1.2.1), (A1.5)+(B1.2.2), (A1.5)+(B1.2.3), (A1.5)+(B1.2.4), (A1.5)+(B1.2.5), (A1.5)+(B1.2.6), (A1.5)+(B1.2.7), (A1.5)+(B1.2.8), (A1.5)+(B1.3.1), (A1.5)+(B1.3.2), (A1.5)+(B1.3.3), (A1.5)+(B1.4.1), (A1.5)+(B1.4.2), (A1.5)+(B1.4.3), (A1.5)+(B1.4.4), (A1.5)+(B1.4.5), (A1.5)+(B1.4.6), (A1.5)+(B1.4.7), (A1.5)+(B1.5.1), (A1.5)+(B1.5.2), (A1.5)+(B1.5.3), (A1.5)+(B1.5.4), (A1.5)+(B1.6.1), (A1.5)+(B1.6.2), (A1.5)+(B1.6.3), (A1.5)+(B1.6.4), (A1.5)+(B1.6.5), (A1.5)+(B1.6.6), (A1.5)+(B1.6.7), (A1.5)+(B1.6.8), (A1.5)+(B1.6.9), (A1.5)+(B1.6.10), (A1.5)+(B1.6.11), (A1.5)+(B1.6.12), (A1.5)+(B1.6.13), (A1.5)+(B1.6.14), (A1.5)+(B1.6.15), (A1.5)+(B1.6.16), (A1.5)+(B1.6.17), (A1.5)+(B1.6.18), (A1.5)+(B1.6.19), (A1.5)+(B1.6.20), (A1.5)+(B1.6.21), (A1.5)+(B1.6.22), (A1.5)+(B1.6.23), (A1.5)+(B1.6.24), (A1.5)+(B1.6.25), (A1.5)+(B1.6.26), (A1.5)+(B1.6.27), (A1.5)+(B1.6.28), (A1.5)+(B1.6.29), (A1.5)+(B1.6.30), (A1.5)+(B1.6.31), (A1.5)+(B1.6.32), (A1.5)+(B1.6.33), (A1.5)+(B1.6.34), (A1.5)+(B1.6.35), (A1.5)+(B1.6.36), (A1.5)+(B1.7.1), (A1.5)+(B1.7.2), (A1.5)+(B1.7.3), (A1.5)+(B1.7.4), (A1.5)+(B1.7.5), (A1.5)+(B1.7.6), (A1.5)+(B1.7.7), (A1.5)+(B1.7.8), (A1.5)+(B1.7.9), (A1.5)+(B2.1.1), (A1.5)+(B2.1.2), (A1.5)+(B2.2.1), (A1.5)+(B2.3.1), (A1.5)+(B2.3.2), (A1.5)+(B2.3.3), (A1.5)+(B2.3.4), (A1.5)+(B2.3.5), (A1.5)+(B2.3.6), (A1.5)+(B2.4.1), (A1.5)+(B2.4.2), (A1.5)+(B2.4.3), (A1.5)+(B2.4.4), (A1.5)+(B2.4.5), (A1.5)+(B2.4.6), (A1.5)+(B2.5.1), (A1.5)+(B2.5.2), (A1.5)+(B2.5.3), (A1.5)+(B2.5.4), (A1.5)+(B2.5.5), (A1.5)+(B2.5.6), (A1.5)+(B2.5.7), (A1.5)+(B2.5.8), (A1.5)+(B2.5.9), (A1.5)+(B2.5.10), (A1.5)+(B2.5.11), (A1.5)+(B2.5.12), (A1.5)+(B2.5.13), (A1.5)+(B2.5.14), (A1.5)+(B2.5.16), (A1.5)+(B2.5.17), (A1.5)+(B2.6.1), (A1.5)+(B2.6.2), (A1.5)+(B2.6.3), (A1.5)+(B2.6.4), (A1.5)+(B2.6.5), (A1.5)+(B2.6.6), (A1.5)+(B2.6.7), (A1.5)+(B2.6.8), (A1.5)+(B2.6.9), (A1.5)+(B2.6.10), (A1.5)+(B2.6.11), (A1.5)+(B2.6.12), (A1.5)+(B2.6.13), (A1.5)+(B2.6.14), (A1.5)+(B3.1.1), (A1.5)+(B3.2.1), (A1.5)+(B3.3.1), (A1.5)+(B3.3.2), (A1.5)+(B3.3.3), (A1.5)+(B3.3.4), (A1.5)+(B3.3.5), (A1.5)+(B3.3.6) and (A1.5)+(B3.3.7), (A2.1)+(B1.1.1), (A2.1)+(B1.1.2), (A2.1)+(B1.1.3), (A2.1)+(B1.1.4), (A2.1)+(B1.1.5), (A2.1)+(B1.2.1), (A2.1)+(B1.2.2), (A2.1)+(B1.2.3), (A2.1)+(B1.2.4), (A2.1)+(B1.2.5), (A2.1)+(B1.2.6), (A2.1)+(B1.2.7), (A2.1)+(B1.2.8), (A2.1)+(B1.3.1), (A2.1)+(B1.3.2), (A2.1)+(B1.3.3), (A2.1)+(B1.4.1), (A2.1)+(B1.4.2), (A2.1)+(B1.4.3), (A2.1)+(B1.4.4), (A2.1)+(B1.4.5), (A2.1)+(B1.4.6), (A2.1)+(B1.4.7), (A2.1)+(B1.5.1), (A2.1)+(B1.5.2), (A2.1)+(B1.5.3), (A2.1)+(B1.5.4), (A2.1)+(B1.6.1), (A2.1)+(B1.6.2), (A2.1)+(B1.6.3), (A2.1)+(B1.6.4), (A2.1)+(B1.6.5), (A2.1)+(B1.6.6), (A2.1)+(B1.6.7), (A2.1)+(B1.6.8), (A2.1)+(B1.6.9), (A2.1)+(B1.6.10), (A2.1)+(B1.6.11), (A2.1)+(B1.6.12), (A2.1)+(B1.6.13), (A2.1)+(B1.6.14), (A2.1)+(B1.6.15), (A2.1)+(B1.6.16), (A2.1)+(B1.6.17), (A2.1)+(B1.6.18), (A2.1)+(B1.6.19), (A2.1)+(B1.6.20), (A2.1)+(B1.6.21), (A2.1)+(B1.6.22), (A2.1)+(B1.6.23), (A2.1)+(B1.6.24), (A2.1)+(B1.6.25), (A2.1)+(B1.6.26), (A2.1)+(B1.6.27), (A2.1)+(B1.6.28), (A2.1)+(B1.6.29), (A2.1)+(B1.6.30), (A2.1)+(B1.6.31), (A2.1)+(B1.6.32), (A2.1)+(B1.6.33), (A2.1)+(B1.6.34), (A2.1)+(B1.6.35), (A2.1)+(B1.6.36), (A2.1)+(B1.7.1), (A2.1)+(B1.7.2), (A2.1)+(B1.7.3), (A2.1)+(B1.7.4), (A2.1)+(B1.7.5), (A2.1)+(B1.7.6), (A2.1)+(B1.7.7), (A2.1)+(B1.7.8), (A2.1)+(B1.7.9), (A2.1)+(B2.1.1), (A2.1)+(B2.1.2), (A2.1)+(B2.2.1), (A2.1)+(B2.3.1), (A2.1)+(B2.3.2), (A2.1)+(B2.3.3), (A2.1)+(B2.3.4), (A2.1)+(B2.3.5), (A2.1)+(B2.3.6), (A2.1)+(B2.4.1), (A2.1)+(B2.4.2), (A2.1)+(B2.4.3), (A2.1)+(B2.4.4), (A2.1)+(B2.4.5), (A2.1)+(B2.4.6), (A2.1)+(B2.5.1), (A2.1)+(B2.5.2), (A2.1)+(B2.5.3), (A2.1)+(B2.5.4), (A2.1)+(B2.5.5), (A2.1)+(B2.5.6), (A2.1)+(B2.5.7), (A2.1)+(B2.5.8), (A2.1)+(B2.5.9), (A2.1)+(B2.5.10), (A2.1)+(B2.5.11), (A2.1)+(B2.5.12), (A2.1)+(B2.5.13), (A2.1)+(B2.5.14), (A2.1)+(B2.5.16), (A2.1)+(B2.5.17), (A2.1)+(B2.6.1), (A2.1)+(B2.6.2), (A1.5)+(B2.6.3), (A2.1)+(B2.6.4), (A2.1)+(B2.6.5), (A2.1)+(B2.6.6), (A2.1)+(B2.6.7), (A2.1)+(B2.6.8), (A2.1)+(B2.6.9), (A2.1)+(B2.6.10), (A2.1)+(B2.6.11), (A2.1)+(B2.6.12), (A2.1)+(B2.6.13), (A2.1)+(B2.6.14), (A2.1)+(B3.1.1), (A2.1)+(B3.2.1), (A2.1)+(B3.3.1), (A2.1)+(B3.3.2), (A2.1)+(B3.3.3), (A2.1)+(B3.3.4), (A2.1)+(B3.3.5), (A2.1)+(B3.3.6) and (A2.1)+(B3.3.7).

The abovementioned application ranges and quantitative ratios here are in each case preferred.

In individual cases, it may be meaningful to combine one or more, preferably one, of the compounds (A) with more than one compound (B) from amongst classes (B1), (B2) and (B3).

Moreover, the combinations according to the invention can be employed together with other active substances, for example from the group of the safeners, fungicides, insecticides and plant growth regulators, or from the group of the additives and formulation auxiliaries conventionally used in crop protection. Additives are, for example, fertilizers and colors.

The combinations according to the invention (=herbicidal compositions) have an outstanding herbicidal activity against a broad spectrum of economically important monocotyledonous and dicotyledonous harmful plants. The active substances also act efficiently on perennial weeds which produce shoots from rhizomes, rootstocks or other perennial organs and which are difficult to control. In this context, it does not matter whether the substances are applied before sowing, pre-emergence or post-emergence. Post-emergence application, or early post-sowing pre-emergence application, is preferred.

Specifically, examples may be mentioned of some representatives of the monocotyledonous and dicotyledonous weed flora which can be controlled by the compounds according to the invention, without the enumeration being a restriction to certain species.

Examples of weed species on which the herbicidal compositions act efficiently are, from amongst the monocots, Avena spp., Alopecurus spp., Brachiaria spp., Digitaria spp., Lolium spp., Echinochloa spp., Panicum spp., Phalaris spp., Poa spp., Setaria spp. and Cyperus species from the annual group and, amongst the perennial species, Agropyron, Cynodon, Imperata and Sorghum and also perennial Cyperus species.

In the case of the dicotyledonous weed species, the spectrum of action extends to species such as, for example, Abutilon spp., Amaranthus spp., Chenopodium spp., Chrysanthemum spp., Galium spp., Ipomoea spp., Kochia spp., Lamium spp., Matricaria spp., Pharbitis spp., Polygonum spp., Sida spp., Sinapis spp., Solanum spp., Stellaria spp., Veronica spp. and Viola spp., Xanthium spp., amongst the annuals, and Convolvulus, Cirsium, Rumex and Artemisia in the case of the perennial weeds.

If the compounds according to the invention are applied to the soil surface before germination, then the weed seedlings are either prevented completely from emerging, or the weeds grow until they have reached the cotyledon stage but then their growth stops, and, eventually, after three to four weeks have elapsed, they die completely.

If the active substances are applied post-emergence to the green parts of the plants, growth likewise stops drastically a very short time after the treatment and the weed plants remain at the growth stage of the point of time of application, or they die completely after a certain time, so that in this manner competition by the weeds, which is harmful to the crop plants, is eliminated at a very early point in time and in a sustained manner.

The herbicidal compositions according to the invention are distinguished by a rapidly commencing and long lasting herbicidal action. As a rule, the rainfastness of the active substances in the combinations according to the invention is advantageous. A particular advantage is that the dosages of the compounds (A) and (B), which are used in the combinations and are effective, can be adjusted to such a low quantity that their soil action is optimally low. This does not only allow them to be employed in sensitive crops in the first place, but groundwater contaminations are virtually avoided. The active-substance combination according to the invention allows the application rate of the active substances required to be reduced considerably.

When herbicides of the type (A)+(B) are used jointly, superadditive (=synergistic) effects are observed. This means that the effect in the combinations exceeds the expected total of the effects of the individual herbicides employed. The synergistic effects allow the application rate to be reduced, a broader spectrum of broad-leaved weeds and grass weeds to be controlled, the herbicidal action to take place more rapidly, the duration of action to be longer, the harmful plants to be controlled better while using only one, or few, applications, and the application period which is possible to be extended. In some cases, use of the compositions also reduces the amount of harmful constituents, such as nitrogen or oleic acid, and their entry into the ground. The abovementioned properties and advantages are necessary under practical weed control conditions to keep agricultural crops free from undesired competing plants and thus to guarantee and/or increase the yields from the qualitative and quantitative point of view. These novel combinations markedly exceed the technical state of the art with a view to the properties described.

While the combinations according to the invention have an outstanding herbicidal activity against monocotyledonous and dicotyledonous weeds, the crop plants are damaged only to a minor extent, or not at all.

Moreover, some of the compositions according to the invention have outstanding growth-regulatory properties on the crop plants. They engage in the plants' metabolism in a regulatory manner and can thus be employed for provoking directed effects on plant constituents and to facilitate harvesting such as for example by triggering desiccation and stunting of growth. Moreover, they are also suitable for the general control and inhibition of undesired vegetative growth without simultaneously destroying the plants. An inhibition of vegetative growth is very important inca large number of monocotyledonous and dicotyledonous crops since lodging can thus be reduced, or prevented completely.

Owing to their herbicidal and plant-growth-regulatory properties, the compositions can be employed for controlling harmful plants in known plant crops, or in tolerant or genetically engineered crop plants still to be developed. As a rule, the transgenic plants are distinguished by particular, advantageous properties, in addition to resistances to the compositions according to the invention, for example, by resistances to plant diseases or pathogens of plant diseases such as particular insects or microorganisms such as fungi, bacteria or viruses. Other particular properties relate, for example, to the harvested material with regard to quantity, quality, storability, composition and specific constituents. Thus, transgenic plants are known whose starch content is increased or whose starch quality is altered, or those where the harvested material has a different fatty acid composition.

Conventional methods of generating novel plants which have modified properties in comparison to plants occurring to date consist, for example, in traditional breeding methods and the generation of mutants. Alternatively, novel plants with altered properties can be generated with the aid of genetic engineering methods (see, for example, EP-A-0221044, EP-A-0131624). For example, the following were described in several cases:

the modification, by genetic engineering, of crop plants with the aim of modifying the starch synthesized in the plant (for example WO 92/11376, WO 92/14827, WO 91/19806), transgenic crop plants which exhibit resistances to other herbicides, for example to sulfonylureas (EP-A-0257993, U.S. Pat. No. 5,013,659), transgenic crop plants with the capability of producing *Bacillus thuringiensis* toxins (Bt toxins), which make the plants resistant to certain pests (EP-A-0142924, EP-A-0193259), transgenic crop plants with a modified fatty acid composition (WO 91/13972).

A large number of techniques in molecular biology with the aid of which novel transgenic plants with modified properties can be generated are known in principle; see, for example, Sambrook et al., 1989, Molecular Cloning, A Laboratory Manual, 2nd Edition, Cold Spring Harbor Laboratory Press, Cold Spring Harbor, N.Y.; or Winnacker "Gene und Klone" [Genes and Clones], VCH Weinheim 2nd Edition 1996 or Christou, "Trends in Plant Science" 1 (1996) 423–431.

To carry out such genetic engineering manipulations, nucleic acid molecules which allow mutagenesis or sequence changes by recombination of DNA sequences can be introduced in plasmids. For example, the abovementioned standard methods allow base changes to be carried out, subsequences to be removed, or natural or synthetic sequences to be added. To connect the DNA fragments to each other, adaptors or linkers may be added to the fragments.

For example, the generation of plant cells with a reduced activity of a gene product can be achieved by expressing at least one corresponding antisense RNA, a sense RNA for achieving a cosuppression effect or by expressing at least one suitably constructed ribozyme which specifically cleaves transcripts of the abovementioned gene product.

To this end, it is possible to use, on the one hand, DNA molecules which encompass the entire encoding sequence of a gene product inclusive of any flanking sequences which may be present, as well as DNA molecules which only encompass portions of the encoding sequence, it being necessary for these portions to be long enough to have an antisense effect on the cells. The use of DNA sequences which have a high degree of homology to the encoding sequences of a gene product, but are not completely identical to them, is also possible.

When expressing nucleic acid molecules in plants, the protein synthesized can be localized in any desired compartment of the plant cell. However, to achieve localization in a particular compartment, it is possible, for example, to link the encoding region with DNA sequences which ensure localization in a particular compartment. Such sequences are known to those skilled in the art (see, for example, Braun et al., EMBO J. 11 (1992), 3219–3227; Wolter et al., Proc. Natl. Acad. Sci. USA 85 (1988), 846–850; Sonnewald et al., Plant J. 1 (1991), 95–106).

The transgenic plant cells can be regenerated by known techniques to give rise to whole plants. In principle, the transgenic plants can be plants of any desired plant species, i.e. not only monocotyledonous, but also dicotyledonous, plants. Thus, transgenic plants can be obtained whose properties are altered by overexpression, suppression or inhibition of homologous (=natural) genes or gene sequences or the expression of heterologous (=foreign) genes or gene sequences.

The invention therefore also relates to a method of controlling undesired vegetation, preferably in plant crops such as cereals (e.g. wheat, barley, rye, oats, rice, corn, millet), which comprises applying one or more herbicides of the type (A) and one or more herbicides of the type (B) to the harmful plants, parts of these plants, or the area under cultivation.

The invention also relates to the use of the novel combinations of compounds (A)+(B) to control harmful plants, preferably in plant crops.

The active substance combinations according to the invention can exist not only as formulation mixes of the two components, if appropriate together with other active substances, additives and/or conventional formulation auxiliaries, which are then applied in the customary manner after dilution with water, but also as so-called tank mixes by jointly diluting the separately formulated, or partially separately formulated, components with water.

Compounds (A) and (B) or their combinations can be formulated in different ways, depending on the biological and/or chemico-physical parameters which prevail. The following are examples of general possibilities for formulations: wettable powders (WP), emulsifiable concentrates (EC), aqueous solutions (SL), emulsions (EW) such as oil-in-water and water-in-oil emulsions, sprayable solutions or emulsions, oil- or water-based dispersions, suspoemulsions, dusts (DP), seed-dressing materials, granules for soil application or for broadcasting, or water dispersible granules (WG), ULV formulations, microcapsules or waxes.

The individual formulation types are known in principle and are described, for example, in: Winnacker-Küchler "Chemische Technologie" [Chemical engineering], Volume 7, C. Hauser Verlag Munich, 4th Edition, 1986; van Valkenburg, "Pesticide Formulations", Marcel Dekker N.Y., 1973; K. Martens, "Spray Drying Handbook", 3rd Ed. 1979, G. Goodwin Ltd. London.

The formulation auxiliaries required, such as inert materials, surfactants, solvents and other additives are also known and are described, for example, in Watkins, "Handbook of Insecticide Dust Diluents and Carriers", 2nd Ed., Darland Books, Caldwell N.J.; H.v. Olphen, "Introduction to Clay Colloid Chemistry"; 2nd Ed., J. Wiley & Sons, N.Y. Marsden, "Solvents Guide", 2nd Ed., lnterscience, N.Y. 1950; McCutcheon's, "Detergents and Emulsifiers Annual", MC Publ. Corp., Ridegewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesellschaft, Stuttgart 1976, Winnacker-Küchler, "Chemische Technologie", Volume 7, C. Hauser Verlag Munich, 4th Edition 1986.

Based on these formulations, combinations with other pesticidally active substances, such as other herbicides, fungicides or insecticides, and with safeners, fertilizers and/or growth regulators, may also be prepared, for example in the form of a readymix or a tank mix.

Wettable powders (sprayable powders) are products which are uniformly dispersible in water and which, besides the active substance, also comprise ionic or nonionic surfactants (wetters, dispersants), for example polyoxethylated alkylphenols, polyethoxylated fatty alcohols or fatty amines, alkanesulfonates or alkylbenzenesulfonates, sodium lignosulfonate, sodium 2,2'-dinaphthylmethane-6,6'-disulfonate, sodium dibutylnaphthalenesulfonate or else sodium oleoylmethyltauride, in addition to a diluent or inert material.

Emulsifiable concentrates are prepared by dissolving the active substance in an organic solvent, for example butanol, cyclohexanone, dimethylformamide, xylene or else higher-boiling aromatic or hydrocarbons with addition of one or more ionic or nonionic surfactants (emulsifiers). Examples of emulsifiers which may be used are: calcium salts of alkylarylsulfonic acids, such as calcium dodecylbenzene sulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan fatty acid esters, polyoxyethylene sorbitan fatty acid esters or polyoxethylene sorbitol esters.

Dusts are obtained by grinding the active substance with finely divided solid materials, for example talc, natural clays such as kaolin, bentonite and pyrophyllite, or diatomateous earth.

Granules can be prepared either by spraying the active substance onto adsorptive, granulated inert material or by applying active substance concentrates to the surface of carriers such as sand, kaolites or granulated inert material with the aid of binders, for example polyvinyl alcohol, sodium polyacrylate or else mineral oils.

Suitable active substances may also be granulated in the manner conventionally used for the production of fertilizer granules, if desired in a mixture with fertilizers. As a rule, water-dispersible granules are prepared by processes such as spray drying, fluidized-bed granulation, disk granulation, mixing with high-speed mixers and extrusion without solid inert material.

As a rule, the agrochemical preparations comprise 0.1 to 99 percent by weight, in particular 2 to 95% by weight, of active substances of the types A and/or B, the following concentrations being customary, depending on the type of formulation: The active substance concentration in wettable powders is, for example, approximately 10 to 95% by weight, the remainder to 100% by weight being composed of customary formulation constituents. In the case of emulsifiable concentrates, the active substance concentration may amount to, for example, 5 to 80% by weight.

Formulations in the form of dusts comprise, in most cases, 5 to 20% by weight of active substance, sprayable solutions approximately 0.2 to 25% by weight of active substance.

In the case of granules such as dispersible granules, the active substance content depends partly on whether the active compound is present in liquid or solid form and on which granulation auxiliaries and fillers are being used. As a rule, the content amounts to between 10 and 90% by weight in the case of the water-dispersible granules.

In addition, the abovementioned active substance formulations may comprise, if appropriate, the conventional adhesives, wetters, dispersants, emulsifiers, preservatives, antifreeze agents, solvents, fillers, colors, carriers, antifoams, evaporation inhibitors, pH regulators or viscosity regulators.

For example, it is known that the effect of glufosinate-ammonium (A1.2) and of its L-enantiomer can be improved by surfactants, preferably by wetters from the series of the alkyl polyglycol ether sulfates which contain, for example, 10 to 18 carbon atoms and which are used in the form of their alkali metal salts or ammonium salts, but also as the magnesium salt, such as sodium $C_{12}/C_{14}$-fatty alcohol diglycol ether sulfate (®Genapol LRO, Hoechst); see EP-A-0476555, EP-A-0048436, EP-A-0336151 or U.S. Pat. No. 4,400,196 and Proc. EWRS Symp. "Factors Affecting Herbicidal Activity and Selectivity", 227–232 (1988). Moreover, it is known that alkyl polyglycol ether sulfates are also suitable as penetrants and synergists for a series of other herbicides, inter alia also herbicides from the series of the imidazolinones; see EP-A-0502014.

For use, the formulations, which are present in commercially available form, are optionally diluted in the customary manner, for example using water in the case of wettable powders, emulsifiable concentrates, dispersions and water-dispersible granules. Preparations in the form of dusts, soil granules, granules for broadcasting and sprayable solutions are usually not diluted further prior to use with other inert substances.

The active substances can be applied to the plants, parts of the plants, seeds of the plants or the area under cultivation (soil of a field), preferably to the green plants and parts of the plants and, if appropriate, additionally to the soil of the field. One possible use is the joint application of the active substances in the form of tank mixes, the concentrated formulations of the individual active substances, in optimal formulations, jointly being mixed with water in the tank and the resulting spray mixture being applied.

A joint herbicidal formulation of the combination according to the invention of the active substances (A) and (B) has the advantage of being easier to apply since the quantities of the components are already presented in the correct ratio to each other. Moreover, the adjuvants in the formulation can be matched optimally to each other, while a tank mix of different formulations may lead to undesired combinations of adjuvants.

A. GENERAL FORMULATION EXAMPLES a) A dust is obtained by mixing 10 parts by weight of an active substance/active substance mixture and 90 parts by weight of talc as inert material and comminuting the mixture in a hammer mill.

b) A wettable powder which is readily dispersible in water is obtained by mixing 25 parts by weight of an active substance/active substance mixture, 64 parts by weight of kaolin-containing quartz as inert material, 10 parts by weight of potassium lignosulfonate and 1 part by weight of sodium oleoylmethyltaurinate as wetter and dispersant, and grinding the mixture in a pinned-disk mill.

c) A dispersion concentrate which is readily dispersible in water is obtained by mixing 20 parts by weight of an active substance/active substance mixture with 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255 to 277° C.), and grinding the mixture in a ball mill to a fineness of below 5 microns.

d) An emulsifiable concentrate is obtained from 15 parts by weight of an active substance/active substance mixture, 75 parts by weight of cyclohexanone as solvent and 10 parts by weight of oxethylated nonylphenol as emulsifier.

e) Water-dispersible granules are obtained by mixing
   75 parts by weight of an active substance/active substance mixture,
   10 parts by weight of calcium lignosulfonate,
   5 parts by weight of sodium lauryl sulfate,
   3 parts by weight of polyvinyl alcohol and
   7 parts by weight of kaolin, grinding the mixture on a pinned-disk mill and granulating the powder in a fluidized bed by spraying on water as granulation liquid.

f) Water-dispersible granules are also obtained by homogenizing and precomminuting, in a colloid mill,
   25 parts by weight of an active substance/active substance mixture,
   5 parts by weight of sodium 2,2'-dinaphthylmethane-6,6'-disulfonate,
   2 parts by weight of sodium oleoylmethyltaurinate,
   1 part by weight of polyvinyl alcohol,
   17 parts by weight of calcium carbonate and
   50 parts by weight of water,
   subsequently grinding the mixture in a bead mill and atomizing and drying the resulting suspension in a spray tower by means of a single-substance model.

BIOLOGICAL EXAMPLES

1. Pre-emergence Effect on Weeds

Seeds or rhizome pieces of monocotyledonous and dicotyledonous weed plants are placed in sandy loam soil in pots and covered with soil. The compositions which are formulated in the form of concentrated aqueous solutions, wettable powders or emulsion concentrates are then applied to the surface of the soil cover in the form of an aqueous solution, suspension or emulsion at an application rate of 600 to 800 l of water/ha (converted), in various dosages. After the treatment, the pots are placed in a greenhouse and kept under good growth conditions for the weeds. After the test plants have emerged, the damage to the plants or the negative effect on the emergence is scored visually after a test period of 3 to 4 weeks by comparison with untreated controls. As shown by the test results, the compositions according to the invention have a good herbicidal pre-emergence activity against a broad spectrum of grass weeds and dicotyledonous weeds.

Scoring and assessment of the synergistic herbicidal effects:

The herbicidal activity of the active substances or active substance mixtures was scored visually with the aid of the treated parcels in comparison with untreated control parcels. Damage to and development of all above-ground parts of plants was recorded here. Scoring was carried out on a percentage scale (100% action=all plants died; 50% action= 50% of the plants and green plant parts died; 0% action=no discernible action=like control parcels. The mean of the scoring values of 4 parcels in each case was taken.

When using the combinations according to the invention, herbicidal actions on a harmful plant species are frequently observed which exceed the formal sum of the actions of the herbicides contained on application on their own. Alternatively, in some cases it can be observed that a lower application rate is needed for the herbicide combination in order to achieve the same action in a harmful plant species in comparison with the individual preparations. Increases in action of increases in effectiveness of this type or savings in application rate are of strong indication of synergistic action.

If the data of the effects observed already exceed the formal total of the data of the experiments with individual applications, then they also exceed Colby's expected value, which is calculated by the formula which follows and which is also considered to be suggestive of synergism (cf. S. R. Colby; in Weeds 15 (1967) pp. 20 to 22):

$$E=A+B-(A\cdot B/100)$$

A, B denote the effect of the active substances A, or in %, for a or b g of a.s./ha; E denotes the expected value in % for a+b g a.s./ha.

At suitable low dosages, the observed data of the experiments show an effect of the combinations above Colby's expected values.

2. Post-emergence Effect on Weeds

Seeds or rhizome pieces of monocotyledonous and dicotyledonous weeds are placed in sandy loam soil in pots, covered with soil and grown in the greenhouse under good growth conditions (temperature, humidity, water supply). Three weeks after sowing, the test plants in the three-leaf stage are treated with the compositions according to the invention. The compositions according to the invention which are formulated as wettable powders or as emulsion concentrates are sprayed in various dosages on the green parts of the plants at an application rate of 600 to 800 l of water/ha (converted). After the test plants have remained in the greenhouse for about 3 to 4 weeks under optimal growth conditions, the effect of the products is scored visually by comparison with untreated controls. When applied post-emergence, too, the compositions according to the invention have a good herbicidal activity against a broad spectrum of economically important grass weeds and broad-leaved weeds.

Frequently, effects of the combinations according to the invention are observed which exceed the formal total of the effects when applying the herbicides individually.

At suitable low dosages, the observed data of the experiments show an effect of the combinations above Colby's expected values. (cf. score figures in Example 1).

3. Herbicidal Effect and Tolerance by Crop Plants (Field Trial)

Crop plants were raised outdoors under natural outdoor conditions on plots in which seeds or rhizome sections of typical harmful plants had been sown or the natural weed infestation was used. The treatment with the compositions according to the invention was carried out after the emergence of the harmful plants and the crop plants, as a rule in the 2 to 4-leaf stage; in some cases (as indicated) the application of individual active substances or active substance combinations was carried out pre-emergence (cf. Example 1) or as a sequence treatment, in some cases pre-emergence and/or post-emergence.

After the application, e.g. 2, 4, 6 and 8 weeks after application, the action of the preparations was scored visually in comparison with untreated controls (cf. score in Example 1). In the field trial as well, the compositions according to the invention had a synergistic herbicidal activity against a broad spectrum of economically important weed grasses and weeds. The comparison showed that the combinations according to the invention usually have more, in some cases considerably more, herbicidal action than the sum of the actions of the individual herbicides and therefore indicate synergism. Moreover, the effects were significantly higher than the expected values according to Colby in significant sections of the scoring period (cf. score in Example 1) and therefore likewise indicate a synergism. The crop plants, however, were not damaged or were only insignificantly damaged as a result of the treatment with the herbicidal compositions.

SPECIFIC EXPERIMENTAL EXAMPLES

In the following tables, in some cases expected values according to Colby are indicated; in each case see expected values E in brackets (E= . . . ).

TABLE 1

Herbicidal action and selectivity in corn

| Active substance(s) | Dose[1] g of A.S./ha | Herbicidal action[2] (%) against Ipomoea purpurea | Damage[2] (%) on corn |
|---|---|---|---|
| (A1.1)[s] | 45 | 78 | 0 |
|  | 60 | 88 | 2 |
|  | 75 | 90 | 4 |
| (B1.2.1) | 1000 | 70 | 0 |
|  | 2000 | 85 | 0 |
|  | 3000 | 90 | 0 |
| (A1.1)[s] + (B1.2.1) | 75 + 1000 | 98 (E = 93) | 0 |

Abbreviations for Table 1:
[1] = Application in each case post-emergence,
[2] = Scoring 3 weeks after application
g of A.S./ha = Grams of active substance ( = 100% active substance) per hectare
(A1.1)[s] = N-[N-(4,6-Dimethoxypyrimidin-2-yl)aminocarbonyl]-2-(dimethylaminocarbonyl)-5-(formylamino)-benzenesulfonamide (A.1.1) in combination with the safener (S1–9),
(S1–9) = Ethyl 5,5-diphenyl-2-isoxazolinecarboxylate
(B1.2.1) = Atrazine

TABLE 2

Herbicidal action and selectivity in corn

| Active substance(s) | Dose[1] g of A.S./ha | Herbicidal action[2] (%) ABUTH | Herbicidal action[2] (%) PHBPU | Damage[2] (%) on corn |
|---|---|---|---|---|
| (A1.1) | 35 (po) | 88 | 45 | 0 |
| (B1.1.2) + (B1.2.1) | 1120 + 1120 (pe) | 43 | 5 | 0 |
| (A1.1) + (B1.1.2) + (B1.2.1) | (1120 + 1120) (pe + 35 (po) | 98 (E = 93) | 92 (E = 50) | 2 |

Abbreviations for Table 2:
[1] = Application in each case post-emergence,
[2] = Scoring 3 weeks after application
(pe) = applied pre-emergence,
(po) = applied post-emergence
g of A.S./ha = Grams of active substance (= 100% active substance) per hectare
(A1.1) N-[N-(4,6-Dimethoxypyrimidin-2-yl)aminocarbonyl]-2-(dimethylaminocarbonyl)-5-(formylamino)-benzenesulfonamide
(B1.2.1) = Atrazine
(B1.1.2) = Metolachlor
ABUTH = Abutilon theophrasti
PHBPU = Pharbitis purpurea

TABLE 3

Herbicidal action and selectivity in corn

| Active substance(s) | Dose[1] g of A.S./ha | Herbicidal action[2] (%) IPOPU | Herbicidal action[2] (%) SIDSP | Damage[2] (%) on corn |
|---|---|---|---|---|
| (A1.1) | 15 | 43 | 0 | 0 |
|  | 30 | 67 | 20 | 0 |
|  | 45 | 70 | 30 | 1 |
|  | 60 | 83 | 50 | 6 |
| (B2.2.1) | 300 | 53 | 70 | 0 |
| (A1.1) + (B2.2.1) | 30 + 300 | 87 (E = 85) | 80(E=76) | 3 |

TABLE 4

Herbicidal action and selectivity in corn

| Active substance(s) | Dose[3] g of A.S./ha | Herbicidal action[4] (%) CHEAL | POLC0 | Damage[4] (%) on corn |
|---|---|---|---|---|
| (A1.1) | 30 | 58 | 20 | 0 |
|  | 45 | 69 | 30 | 0 |
|  | 60 | 85 | 30 | 0 |
| (B2.2.1) | 300 | 75 | 45 | 0 |
| (A1.1) + (B2.2.1) | 45 + 300 | 98 (E = 92) | 80 (30 + 45) | 0 |

Abbreviations for Tables 3 and 4, see Table 2 and additionally:
[1], [3] = Application in each case post-emergence
[2] = Scoring 6 weeks after application
[4] = Scoring 40 days after application
(B2.2.1) = Bromoxynil
CHEAL = Chenopodium album
POLCO = Polygonum convolvulus
IPOPU = Ipomoea purpureum
SIDSP = Sida spinosa

TABLE 5

Herbicidal action and selectivity in corn

| Active substance(s) | Dose[1] g of A.S./ha | Herbicidal action[2] (%) against SIDSP | Damage[2] (%) on corn |
|---|---|---|---|
| (A1.1) | 15 | 0 | 0 |
|  | 30 | 20 | 0 |
|  | 45 | 30 | 1 |
|  | 60 | 50 | 6 |
| (B2.3.3) | 900 | 10 | 0 |
| (A1.1) + (B2.3.3) | 30 + 900 | 80 (20 + 10) | 2 |

Abbreviations for Table 5, see Table 2 and additionally:
[1] = Application in each case post-emergence,
[2] = Scoring 3 weeks after application
(B2.3.3) = Pyridate
SIDSP = Sida spinosa

TABLE 6

Herbicidal action and selectivity in corn

| Active substance(s) | Dose[1] g of A.S./ha | Herbicidal action[2] (%) against AGRRE | Damage[2] (%) on corn |
|---|---|---|---|
| (A1.1)[s] | 30 | 0 | 0 |
|  | 45 | 0 | 0 |
|  | 60 | 5 | 5 |
| (B2.4.4) | 2.5 | 0 | 10 |
|  | 5 | 10 | 20 |
|  | 7.5 | 10 | 30 |
| (A1.1)[s] + (B2.4.4) | 30 + 2.5 | 85 (0 + 0) | 0 |
|  | 30 + 5 | 90 (0 + 10) | 7 |

Abbreviations for Table 6, see Table 1 and additionally:
(B2.4.4) = Iodosulfuron-methyl
AGRRE = Agropyron repens

TABLE 7

Herbicidal action and selectivity in corn

| Active substance(s) | Dose[1] g of A.S./ha | Herbicidal action[2] (%) against AMASP | Damage[2] (%) on corn |
|---|---|---|---|
| (A1.1) | 15 | 0 | 0 |
|  | 30 | 38 | 0 |
|  | 45 | 60 | 1 |
|  | 60 | 70 | 6 |

TABLE 7-continued

Herbicidal action and selectivity in corn

| Active substance(s) | Dose[1] g of A.S./ha | Herbicidal action[2] (%) against AMASP | Damage[2] (%) on corn |
|---|---|---|---|
| (B2.4.5) | 2.5 | 36 | 1 |
|  | 5 | 75 | 1 |
| (A1.1) + (B2.4.5) | 15 + 2.5 | 78 (0 + 36) | 2 |
|  | 15 + 5 | 85 (0 + 75) | 5 |

Abbreviations for Table 7, see Tables 2 and 6 and additionally:
AMASP = Amaranthus spinosus

TABLE 8

Herbicidal action

| Active substance(s) | Dose[1] g of A.S./ha | Herbicidal action[20] (%) against Avena sterilis | Chrysanthemum coronarium |
|---|---|---|---|
| (A1.1) | 60 | 83 | 20 |
| (B3.1.1) | 270 | 10 | 10 |
|  | 450 | 30 | 25 |
| (A1.1) + (B3.1.1) | 60 + 270 | 94 (83 + 10) | 83 |

Abbreviations for Table 8:
[1] = Application in each case post-emergence,
[2] = Scoring 46 days after application
(A1.1) = see Table 2
(B3.1.1) = Glufosinate monoammonium salt

TABLE 9

Herbicidal action and selectivity in corn

| Active substance(s) | Dose[1] g of A.S./ha | Herbicidal action[2] (%) ECHCG | CHEAL | Damage[2] (%) on corn |
|---|---|---|---|---|
| (A1.1) | 120 | 65 | 65 | 10 |
|  | 60 | 35 | 40 | 10 |
|  | 30 | 5 | 25 | 10 |
|  | 15 | 0 | 5 | 10 |
| (B1.3.1) | 60 | 89 | 90 | 0 |
|  | 30 | 88 | 65 | 0 |
|  | 15 | 88 | 55 | 0 |
| (A1.1) + (B1.3.1) | 30 + 30 | 90 (E = 89) | 90 (E = 73) | 10 |
|  | 15 + 30 | 99 (0 + 88) | 88 (5 + 65) | 10 |
|  | 30 + 15 | 97 (5 + 88) | 80 (E = 66) | 15 |
| (B1.1.2) | 2000 | 55 | 0 | 0 |
|  | 1000 | 45 | 0 | 0 |
|  | 500 | 40 | 0 | 0 |
| (A1.1) + (B1.1.2) | 30 + 1000 | 98 (5 + 45) | 90 (25 + 0) | 15 |
|  | 15 + 1000 | 98 (0 + 45) | 90 (5 + 0) | 5 |
|  | 30 + 500 | 93 (5 + 40) | 83 (25 + 0) | 10 |

Abbreviations for Table 9:
[1] = Scoring 3 weeks after application
[2] = application in each case post-emergence
g of A.S./ha = Grams of active substance (= 100% active substance) per hectare
(A1.1) = see Table 2
(B1.1.2) = Metolachlor
(B1.3.1) = Nicosulfuron
CHEAL = Chenopodium album
ECHCG = Echinochloa crus-galli

TABLE 10

Herbicidal action and selectivity in corn

| Active substance(s) | Dose[1] g of A.S./ha | Herbicidal action[2] (%) ECHCG | SOLNI | XANOR | Damage[2] (%) on corn |
|---|---|---|---|---|---|
| (A1.1) | 120 | 65 | 90 | 60 | 10 |
|  | 60 | 35 | 90 | 60 | 10 |
|  | 30 | 5 | 83 | 55 | 10 |
|  | 15 | 0 | 65 | 45 | 10 |
| (B1.3.2) | 12 | 97 | 60 | — | 0 |
|  | 6 | 93 | 45 |  | 0 |
|  | 3 | 93 | 35 |  | 0 |
| (A1.1) + (B1.3.2) | 30 + 6 | 99 (5 + 93) | 98 (E = 91) | — | 15 |
|  | 15 + 6 | 99 (0 + 93) | 97 (E = 81) |  | 15 |
|  | 30 + 3 | 99 (5 + 93) | 98 (E = 89) |  | 15 |
| (B2.4.1) | 2000 | 65 | — | 10 | 0 |
|  | 1000 | 65 |  | 0 | 8 |
|  | 500 | 65 |  | 0 | 8 |
| (A1.1) + (B2.4.1) | 30 + 1000 | 83 (5 + 65) | — | 60 (55 + 0) | 15 |
|  | 15 + 1000 | 85 (0 + 65) |  | 60 (45 + 0) | 5 |
|  | 30 + 500 | 80 (5 + 65) |  | 70 (55 + 0) | 10 |

Abbreviations for Table 10:
[1] = Scoring 3 weeks after application
[2] = application in each case post-emergence
g of A.S./ha = Grams of active substance (= 100% active substance) per hectare
(A1.1) = see Table 2
(B1.3.2) = Rimsulfuron
(B2.4.1) = Pendimethalin
ECHCG = Echinochloa crus-galli
YANOR = Xanthium orientalis

TABLE 11

Herbicidal action and selectivity in corn

| Active substance(s) | Dose[1] g of A.S./ha | Herbicidal action[2] (%) ECHCG | SETVI | Damage[2] (%) on corn |
|---|---|---|---|---|
| (A1.1) | 120 | 65 | 89 | 10 |
|  | 60 | 35 | 83 | 10 |
|  | 30 | 5 | 75 | 10 |
|  | 15 | 0 | 55 | 10 |
| (B1.2.1) | 2000 | 78 | 10 | 10 |
|  | 1000 | 35 | 0 | 0 |
|  | 500 | 20 | 0 | 0 |
| (A1.1) + (B1.2.1) | 30 + 1000 | 85 (5 + 35) | 90 (75 + 0) | 0 |
|  | 15 + 1000 | 80 (0 + 35) | 85 (55 + 0) | 0 |
|  | 30 + 500 | 75 (5 + 20) | 83 (75 + 0) | 0 |
| (B1.4.2) | 600 | 97 | 90 | 0 |
|  | 300 | 83 | 40 | 0 |
|  | 150 | 80 | 20 | 0 |
| (A1.1) + (B1.4.2) | 30 + 300 | 93 (5 + 83) | 99 (E = 80) | 0 |
|  | 15 + 300 | 90 (0 + 83) | 97 (55 + 40) | 0 |
|  | 30 + 150 | 88 (5 + 80) | 98 (75 + 20) | 0 |

Abbreviations for Table 11:
[1] = Scoring 3 weeks after application
[2] = application in each case post-emergence
g of A.S./ha = Grams of active substance (= 100% active substance) per hectare
(A1.1) = see Table 2
(B1.2.1) = Atrazine
(B1.4.2) = Sulcotrione
ECHCG = Echinochloa crus-galli
SETVI = Setaria viridis

TABLE 12

Herbicidal action and selectivity in corn

| Active substance(s) | Dose[1] g of A.S./ha | Herbicidal action[2] (%) ECHCG | POLCO | Damage[2] (%) on corn |
|---|---|---|---|---|
| (A1.1) | 120 | 65 | 30 | 10 |
|  | 60 | 35 | 30 | 10 |
|  | 30 | 5 | 25 | 10 |
|  | 15 | 0 | 5 | 10 |
| (B3.2.1) | 1000 | 98 | 82 | — |
|  | 500 | 83 | 78 |  |
|  | 250 | 73 | 55 |  |
| (A1.1) + (B3.2.1) | 30 + 500 | 100 (5 + 83) | 93 (E = 84) | — |
|  | 30 + 250 | 100 (5 + 73) | 83 (25 + 55) |  |
|  | 15 + 250 | 100 (0 + 73) | 78 (5 + 55) |  |
| (B1.3.3) | 40 | 5 | 68 | 15 |
|  | 20 | 3 | 63 | 0 |
|  | 10 | 0 | 60 | 0 |
| (A1.1) + (B1.3.3) | 30 + 20 | 55 (5 + 3) | 90 (25 + 63) | 0 |
|  | 15 + 20 | 50 (0 + 3) | 80 (5 + 63) | 0 |
|  | 30 + 10 | 45 (5 + 0) | 88 (25 + 60) | 5 |
| (B1.2.5) | 200 | 89 | 80 | 25 |
|  | 100 | 75 | 65 | 20 |
|  | 50 | 5 | 45 | 15 |
| (A1.1) + (B1.2.5) | 30 + 100 | 92 (5 + 75) | 93 (25 + 65) | 0 |
|  | 15 + 100 | 95 (0 + 75) | 90 (5 + 65) | 0 |
|  | 30 + 50 | 83 (5 + 5) | 75 (25 + 45) | 0 |

Abbreviations for Table 12:
[1] = Scoring 3 weeks after application
[2] = application in each case post-emergence
g of A.S./ha = Grams of active substance (= 100% active substance) per hectare
(A1.1) = see Table 2
(B3.2.1) = Glyphosate-isopropylammonium
(B1.3.3) = Primisulfuron
(B1.2.5) = Metribuzin
ECHCG = Echinochloa crus-galli
POLCO = Polygonum convolvulus

TABLE 13

Herbicidal action and selectivity in corn

| Active substance(s) | Dose[1] g of A.S./ha | Herbicidal action[2] (%) EPHHL | Damage[2] (%) on corn |
|---|---|---|---|
| (A1.1) | 30 | 70 | 8 |
| (B1.4.4) | 100 | 63 | 5 |
|  | 150 | 73 | 13 |
| (A1.1) + (B1.4.4) | 30 + 50 | 90 | 8 |

[1] = Scoring 3 weeks after application
[2] = Application in each case post-emergence
g of A.S./ha = Grams of active substance per hectare
(A1.1) = see Table 2
(B1.4.4) = 2-(4-Mesyl-2-nitrobenzoyl)cyclohexane-1,3-dione (mesotrione)
EPHHL = Euphorbia heterophylla

TABLE 14

Herbicidal action and selectivity in corn

| Active substance(s) | Dose[1] g of A.S./ha | Herbicidal action[2] (%) Polygonum convolvulus | Damage[2] (%) on corn |
|---|---|---|---|
| (A1.1) | 30 | 50 | 8 |
|  | 15 | 35 | 6 |
|  | 7.5 | 10 | 0 |
| (B1.2.3) = Cyanazin | 2200 | 75 | 15 |
|  | 1100 | 55 | 12 |
|  | 550 | 20 | 5 |

TABLE 14-continued

Herbicidal action and selectivity in corn

| Active substance(s) | Dose[1] g of A.S./ha | Herbicidal action[2] (%) Polygonum convolvulus | Damage[2] (%) on corn |
|---|---|---|---|
| (A1.1) + (B1.2.3) | 7.5 + 2200 | 96 (10 + 75) | 12 |
| | 7.5 + 1100 | 78 (10 + 55) | 9 |

Abbreviations for Table 14:
[1] = Scoring 4 weeks after application
[2] = Application in each case post-emergence
(A1.1) = see Table 2

TABLE 15

Herbicidal action and selectivity in corn

| Active substance(s) | Dose[1] g of A.S./ha | Herbicidal action[2] (%) Polygonum convolvulus | Damage[2] (%) on corn |
|---|---|---|---|
| (A1.1) | 30 | 65 | 6 |
| | 15 | 35 | 3 |
| | 7.5 | 10 | 1 |
| (B1.1.4) = Dimethenamid | 900 | 40 | 0 |
| | 450 | 20 | 0 |
| (B1.2.7) = Fluthiamid | 600 | 25 | 0 |
| (B1.5.1) = Metosulam | 20 | 55 | 0 |
| (A1.1) + (B1.1.4) | 30 + 450 | 85 (65 + 20) | 5 |
| | 7.5 + 900 | 80 (10 + 40) | 1 |
| (A1.1) + (B1.2.7) | 30 + 600 | 93 (65 + 25) | 5 |
| | 7.5 + 600 | 75 (10 + 25) | 3 |
| (A1.1) + (B1.5.1) | 15 + 20 | 93 (35 + 55) | 12 |
| | 7.5 + 20 | 75 (10 + 55) | 6 |

Abbreviations for Table 15:
[1] = Scoring 4 weeks after application
[2] = Application in each case post-emergence
(A1.1) = see Table 2

TABLE 16

Herbicidal action and selectivity in corn

| Active substance(s) | Dose[1] g of A.S./ha | Herbicidal action[2] (%) Convolvulus arvensis | Damage[2] (%) on corn |
|---|---|---|---|
| (A1.1) | 60 | 65 | 8 |
| | 30 | 40 | 6 |
| | 15 | 30 | 4 |
| (B2.5.2) = MCPA | 1500 | 85 | 10 |
| | 750 | 50 | 6 |
| | 375 | 30 | 0 |
| (A1.1) + (B2.5.2) | 30 + 750 | 95 (40 + 50) | 8 |
| | 30 + 375 | 80 (40 + 30) | 6 |
| | 15 + 750 | 85 (30 + 50) | 7 |
| | 60 + 375 | 98 (65 + 30) | 9 |

Abbreviations for Table 16:
[1] = Scoring 4 weeks after application
[2] = Application in each case post-emergence
(A1.1) = see Table 2

TABLE 17

Herbicidal action and selectivity in corn

| Active substance(s) | Dose[1] g of A.S./ha | Herbicidal action[2] (%) Digitaria sanguinalis | Damage[2] (%) on corn |
|---|---|---|---|
| (A1.1) | 60 | 75 | 8 |
| | 30 | 55 | 6 |
| | 15 | 35 | 5 |
| (B1.1.1) = Alachlor | 2000 | 65 | 0 |
| | 1000 | 50 | 0 |
| | 500 | 40 | 0 |
| (A1.1) + (B1.1.1) | 15 + 1000 | 93 (35 + 50) | 5 |
| | 30 + 500 | 97 (55 + 40) | 6 |
| (B1.1.3) = Acetochlor | 2000 | 85 | 0 |
| | 1000 | 50 | 0 |
| | 500 | 25 | 0 |
| (A1.1) + (B1.1.3) | 30 + 500 | 89 (55 + 25) | 2 |
| | 15 + 500 | 78 (35 + 25) | 1 |
| | 15 + 1000 | 92 (35 + 50) | 4 |

Abbreviations for Table 17:
[1] = Scoring 4 weeks after application
[2] = Application in each case post-emergence
(A1.1)[s] = see Table 1

TABLE 18

Herbicidal action and selectivity in corn

| Active substance(s) | Dose[1] g of A.S./ha | Herbicidal action[2] (%) Digitaria sanguinalis | Damage[2] (%) on corn |
|---|---|---|---|
| (A1.1)[s] | 45 | 7.3 | 8 |
| | 22.5 | 45 | 6 |
| | 12.5 | 28 | 5 |
| (B1.4.6) = Isoxachlortole | 25 | 45 | 12 |
| | 12.5 | 30 | |
| (A1.1)[s] + (B1.4.6) | 12.5 + 25 | 78 (28 + 45) | 15 |
| | 12.5 + 12.5 | 75 (28 + 30) | 18 |

Abbreviations for Table 18:
[1] = Scoring 4 weeks after application
[2] = Application in each case post-emergence
(A1.1)[s] = see Table 1

TABLE 19

Herbicidal action and selectivity in corn

| Active substance(s) | Dose[1] g of A.S./ha | Herbicidal action[2] (%) Cirsium avense | Damage[2] (%) on corn |
|---|---|---|---|
| (A1.1)[s] | 60 | 65 | 8 |
| | 30 | 35 | 6 |
| | 15 | 20 | 5 |
| (B2.3.6) = Clopyralid | 120 | 88 | 3 |
| | 60 | 60 | 0 |
| | 30 | 20 | 0 |
| (A2.1)[s] + (B2.3.6) | 30 + 30 | 75 (35 + 20) | 2 |
| | 30 + 60 | 98 (35 + 60) | 5 |
| | 60 + 30 | 88 (65 + 20) | 4 |

Abbreviations for Table 19:
[1] = Scoring 3 weeks after application
[2] = Application in each case post-emergence
(A1.1)[s] = see Table 1

TABLE 20

Herbicidal action and selectivity in corn

| Active substance(s) | Dose[1] g of A.S./ha | Herbicidal action[2] (%) Ipomoea hederacea | Damage[2] (%) on corn |
|---|---|---|---|
| (A1.1) | 60 | 75 | 12 |
| | 30 | 60 | 10 |
| | 15 | 10 | 8 |

TABLE 20-continued

Herbicidal action and selectivity in corn

| Active substance(s) | Dose[1] g of A.S./ha | Herbicidal action[2] (%) Ipomoea hederacea | Damage[2] (%) on corn |
|---|---|---|---|
| (B1.4.3) = Dicamba | 240 | 85 | 8 |
| | 120 | 75 | 6 |
| | 60 | 40 | 5 |
| (A1.1) + (B1.4.3) | 15 + 60 | 75 (25 + 40) | 8 |
| | 15 + 120 | 90 (10 + 75) | 10 |
| | 30 + 60 | 95 (60 + 30) | 9 |

Abbreviations for Table 20:
[1] = Scoring 3 weeks after application
[2] = Application in each case post-emergence
(A1.1) = see Table 2

TABLE 21

Herbicidal action and selectivity in corn

| Active substance(s) | Dose[1] g of A.S./ha | Herbicidal action[2] (%) Chenopodium album | Damage[2] (%) on corn (IR) |
|---|---|---|---|
| (A1.1)$^s$ | 60 | 85 | 12 |
| | 30 | 60 | 8 |
| | 15 | 35 | 6 |
| (B3.3.2) Imazethapyr | 70 | 65 | 8 |
| | 50 | 40 | 6 |
| | 30 | 25 | 4 |
| (A1.1)$^s$ + (B3.3.2) | 30 + 30 | 93 (60 + 25) | 12 |
| | 15 + 30 | 78 (35 + 25) | 6 |
| | 15 + 50 | 83 (35 + 40) | 8 |

Abbreviations for Table 21:
[1] = Scoring 4 weeks after application
[2] = Application in each case post-emergence
(A1.1)$^s$ = see Table 1
Corn (IR) = Imidazolinone-resistant corn

TABLE 22

Herbicidal action and selectivity in corn

| Active substance(s) | Dose[1] g of A.S./ha | Herbicidal action[2] (%) Lolium multiflorum | Damage[2] (%) on corn (SR) |
|---|---|---|---|
| (A1.1)$^s$ | 50 | 85 | 10 |
| | 25 | 60 | 8 |
| | 12.5 | 30 | 5 |
| (B1.6.33) = Sethoxidim | 400 | 88 | 3 |
| | 200 | 62 | 2 |
| | 100 | 35 | 0 |
| (A1.1)$^s$ + (B1.6.33) | 12.5 + 100 | 78 (30 + 35) | 3 |
| | 12.5 + 200 | 95 (30 + 62) | 5 |
| | 25 + 100 | 97 (60 + 35) | 8 |

Abbreviations for Table 22:
[1] = Scoring 4 weeks after application
[2] = Application in each case post-emergence
(A1.1)$^s$ = see Table 1
Corn (SR) = Sethoxidime-resistant corn

TABLE 23

Herbicidal action

| Active substance(s) | Dose[1] g of A.S./ha | Herbicidal action[2] (%) Setaria viridis |
|---|---|---|
| (A1.1) | 30 | 75 |
| | 15 | 45 |
| | 7.5 | 25 |
| (B1.7.5) = Diclofop-methyl | 720 | 65 |
| (A1.1) + (B1.7.5) | 7.5 + 720 | 93 (25 + 65) |

Abbreviations for Table 23:
[1] = Scoring 4 weeks after application
[2] = Application in each case post-emergence
(A1.1) = see Table 2

TABLE 24

Herbicidal action and selectivity in rice

| Active substance(s) | Dose[1] g of A.S./ha | Herbicidal action[2] (%) Brachiaria plantophylla | Damage[2] (%) on rice |
|---|---|---|---|
| A) (A1.1) | 45 | 65 | 25 |
| | 22.5 | 45 | 15 |
| (B1.6.27) = Fenoxa-prop-p-ethyl | 60 | 70 | 8 |
| | 30 | 30 | 0 |
| (A1.1) + (B1.6.27) | 22.5 + 30 | 83 (45 + 30) | 22 |
| (B2.5.8) = Ethoxy-sulfuron | 60 | 20 | 0 |
| | 30 | 0 | 0 |
| (A1.1) + (B2.5.8) | 22.5 + 30 | 50 (45 + 0) | 18 |
| (B1.6.11) = Anilofos | 450 | 35 | 8 |
| (A1.1) + (B1.6.11) | 22.5 + 450 | 83 (45 + 35) | 28 |

Abbreviations for Table 24:
[1] = Scoring 6 weeks after application
[2] = Application in each case post-emergence
(A1.1) = see Table 2

TABLE 25

Herbicidal action and selectivity in wheat

| Active substance(s) | Dose[1] g of A.S./ha | Herbicidal action[2] (%) Polygonus convolvulus | Damage[2] (%) on wheat |
|---|---|---|---|
| (A1.1) | 30 | 65 | 85 |
| | 15 | 25 | 65 |
| (B2.6.4) = Amidosulfuron | 30 | 55 | 0 |
| | 15 | 35 | 0 |
| (A1.1) = (B2.6.4) | 15 + 30 | 72 (25 + 35) | 75 |

Abbreviations for Table 25:
[1] = Scoring 4 weeks after application
[2] = Application in each case post-emergence
(A1.1) = see Table 2

What is claimed is:

1. A synergistic herbicide combination having a synergistic effective amount of components (A) and (B), where (A) is one or more herbicides selected from the group consisting of the formula (I) and their salts

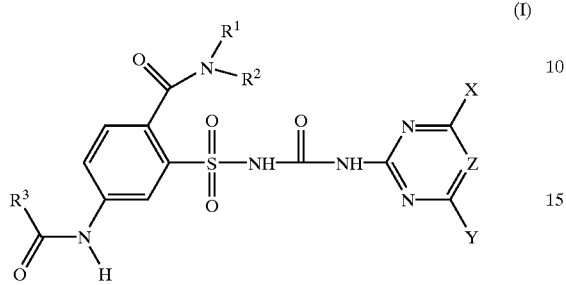

(I)

in which
R$^1$ is hydrogen or (C$_1$-C$_4$)alkyl,
R$^2$ is hydrogen or (C$_1$-C$_4$)alkyl,
R$^3$ is H, (C$_1$-C$_4$)alkyl, (C$_1$-C$_4$)alkoxy, (C$_2$-C$_4$) alkenoxy, (C$_2$-C$_4$)alkynoxy, (C$_3$-C$_6$)cycloalkyl, each of the 5 last-mentioned radicals being unsubstituted or substituted by one or more radicals from the group consisting of halogen, cyano, (C$_1$-C$_4$) alkoxy and (C$_1$-C$_4$)alkylsulfonyl,
one of the radicals X and Y is halogen, (C$_1$-C$_4$)alkyl, (C$_1$-C$_4$)alkoxy, (C$_1$-C$_4$)alkylthio, where each of the three last-mentioned radicals is unsubstituted or substituted by one or more radicals from the group consisting of halogen, (C$_1$-C$_4$)alkyl, (C$_1$-C$_4$)alkoxy, (C$_1$-C$_4$)alkylthio,
and the other of the radicals X and Y is (C$_1$-C$_4$)alkyl, (C$_1$-C$_4$)alkoxy or (C$_1$-C$_4$)alkylthio, where each of the three last-mentioned radicals is unsubstituted or substituted by one or more radicals from the group consisting of halogen, (C$_1$-C$_4$)alkoxy and (C$_1$-C$_4$) alkylthio,
Z is CH, and (B) one or more herbicides from the group consisting of alachlor, metolachlor, acetochlor, dimethenamid, pethoxamid, atrazine, simazine, syanazine, terbuthylazine, metribuzin, isoxaflutole, fluthiamide, terbutryn, nicosulfuron, rimsulfuron, primisulfuron, pendimethalin, sulcotrione, dicamba, mesotrione, linuron, isoxachlortole, benoxacor, metosulam, flumetsulam, cloransulam, florasulam, molinate, thiobencarb, quinchlorac, propanil, pyribenzoxim, butachlor, pretilachlor, clomazone, oxadiargyl, oxaziclomefone, anilofos, cafenstrole, mefenacet, fentrazamid, thiazopyr, triclopyr, oxadiazone, esprocarb, pyributicarb, azimsulfuron, thenylchlor, pentoxazone, pyriminobac, quizalofop/quizalofop-P, fenoxacrop/fenoxaprop-P, fluazifop/fluazifop-P, haloxyfop/haloxyfop-P, propaquizafop, clodinafop, cyhalofop, sethoxydim, cycloxydim, clethodim, clefoxidim, isoproturon, chlortuloron, prosulfocarb, isopropyl 5-(4-bromo-1-methyl-5-(trifluoromethyl)-1H-pyrazol-3-yl)-2-chloro-4-fluorobenzoate, diclofop/diclofop-P, imazamethabenz, triasulfuron, flupyrsulfuron, a compound of the formula (III) or its salts,

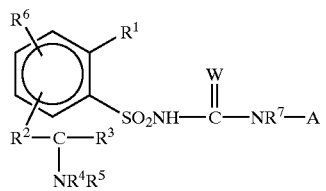

(III)

in which
R$^1$ is CO—Q—R$^8$,
R$^2$ and R$^3$ independently of one another are H or (C$_1$-C$_4$)alkyl,
R$^4$ is H, (C$_1$-C$_8$) alkyl which is unsubstituted or is substituted by one or more radicals from the group consisting of halogen, (C$_1$-C$_4$) alkoxy, (C$_1$-C$_4$) alkylthio, (C$_1$-C$_4$) alkylsulfinyl, (C$_1$-C$_4$) alkylsulfonyl, ((C$_1$-C$_4$)alkoxy)carbonyl and CN, or is (C$_3$-C$_6$)alkenyl which is unsubstituted or is substituted by one or more halogen atoms, or is hydroxyl, (C$_1$-C$_4$) alkoxy, ((C$_1$-C$_4$) alkyl)carbonyl or (C$_1$-C$_4$) alkylsulfonyl, each of the three latter radicals being unsubstituted or unsubstituted in the alkyl moiety by one or more halogen atoms or by (C$_1$-C$_4$)alkoxy or (C$_1$-C$_4$)alkylthio, or is phenylsulfonyl in which the phenyl radical is unsubstituted or substituted, and
R$^5$ is (C$_1$-C$_4$) alkylsulfonyl or (C$_3$-C$_6$) alkenylsulfonyl, each of the two latter radical being unsubstituted or substituted by one or more halogen atoms or by (C$_1$-C$_4$)alkoxy or (C$_1$-C$_4$)alkylthio, or is phenylsulfonyl or phenylcarbonyl, the phenyl radical in each of the two latter radicals being unsubstituted or substituted, or is mono- or di-((C$_1$-C$_4$)alkyl) aminosulfonyl or ((C$_1$-C$_6$)alkyl)carbonyl, each of the three latter radicals being unsubstituted or substituted by one or more radicals from the group consisting of halogen, (C$_1$-C$_4$)alkoxy, (C$_1$-C$_4$) alkoxy, (C$_1$-C$_4$)alkylthio, (C$_1$-C$_4$)alkylsulfinyl, (C$_1$-C$_4$) alkylsulfonyl, ((C$_1$-C$_4$)alkyl)carbonyl, ((C$_1$-C$_4$)alkoxy)carbonyl and CN, or is formyl, a group of the formula —CO—CO—R' in which R'=H, OH, (C$_1$-C$_4$)alkoxy or (C$_1$-C$_4$) alkyl, or is ((C$_3$-C$_6$) Cycloalkyl)carbonyl, ((C$_2$-C$_6$)alkenyl) carbonyl or ((C$_2$-C$_6$) alkynyl)carbonyl, each of the three latter radicals being unsubstituted or substituted by one or more halogen atoms, or is a group of the formula

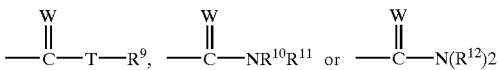

or
R$^4$ and R$^5$ together are a chain of the formula (—CH$_2$)$_m$B— or —B$^1$—(CH$_2$)$_{m1}$—B—, the chain being unsubstituted or substituted by one or more (C$_1$-C$_3$) alkyl radicals and m being 3 or 4 or m$^1$ being 2 or 3, and
W is an oxygen or sulfur atom (i.e. O or S);
B and B$^1$ independently of one another are SO$_2$ or CO;
Q is O, S or —NR$^{13}$—,
T is O or S,
R$^6$ is H, (C$_1$-C$_4$)alkyl, (C$_1$-C$_4$)alkoxy, ((C$_1$-C$_4$)alkyl) carbonyl or ((C$_1$-C$_4$) alkoxy)carbonyl, each of the 4 latter radicals being unsubstituted or substituted in the alkyl moiety by one or more halogen atoms, or is halogen, $NO_2$ or CN, $R^7$ is H or $CH_3$, $R^8$ is H, $(C_1-C_4)$ alkyl, $(C_3-C_4)$alkenyl or $(C_3-C_4)$ alkynyl, each of the three latter radicals being unsubstituted or substituted by one or more radicals from the group consisting of halogen, $(C_1-C_4)$ alkoxy, $(C_1-C_4)$alkylthio, $((C_1-C_4)$alkyl)carbonyl and $((C_1-C_4)$alkoxy) carbonyl, $R^9$ is $(C_1-C_4)$ alkyl, $(C_3-C_4)$alkenyl, $(C_3-C_4)$ alkynyl, each of the three latter radicals being unsubstituted or substituted by one or more radicals from the group consisting of halogen, $(C_1-C_4)$alkoxy, $(C_1-C_4)$ alkylthio, $((C_1-C_4)$alkyl)carbonyl and $((C_1-C_4)$ alkoxy)carbonyl, $R^{10}$ and $R^{11}$ independently of one another are H, $(C_1-C_4)$alkyl, $(C_3-C_4)$ alkenyl or $(C_3-C_4)$alkynyl, each of the three latter radicals being unsubstituted or substituted by one or more radicals from the group consisting of halogen, $(C_1-C_4)$alkoxy, $(C_1-C_4)$ alkylthio, $((C_1-C_4)$ alkoxy)carbonyl, the radicals $R^{12}$ together with the nitrogen atom are a heterocyclic ring having 5 or 6 ring members, which may contain further heteroatoms from the group consisting of N, O and S in the possible oxidation states and is unsubstituted or is substituted by $(C_1-C_4)$alkyl or the oxo group, or is benzo-fused, $R^{13}$ is H, $(C_1-C_4)$ alkyl, $(C_3-C_4)$ alkenyl or $(C_3-C_4)$ alkynyl, each of the three latter radicals being unsubstituted or substituted by one or more radicals from the group consisting of halogen, $(C_1-C_4)$alkoxy and $(C_1-C_4)$alkylthio, A is a radical of the formula

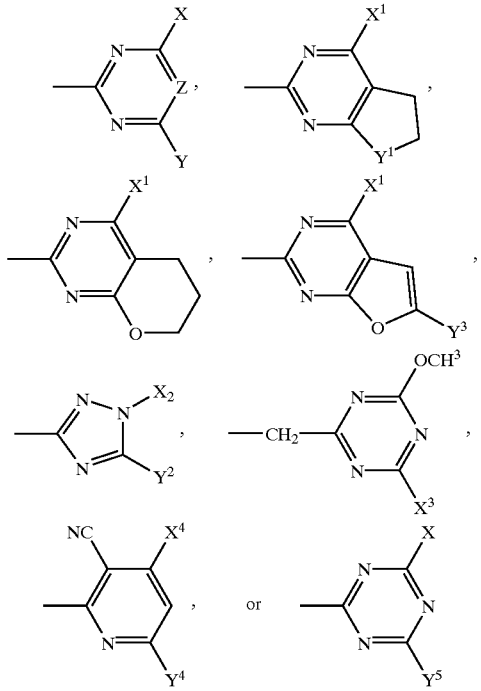

one of the radicals X and Y is hydrogen, halogen, $(C_1-C_3)$alkyl or $(C_1-C_3)$ alkoxy, the two latter radicals being unsubstituted or being mono- or polysubstituted by halogen or monosubstituted by $(C_1-C_3)$ alkoxy, and the other of the radicals X and Y is hydrogen, $(C_1-C_3)$alkyl, $(C_1-C_3)$alkoxy or $(C_1-C_3)$ alkylthio, the three latter alkyl-containing radicals being unsubstituted or mono- or polysubstituted by halogen or mono- or disubstituted by $(C_1-C_3)$ alkoxy or $(C_1-C_3)$alkylthio, or is a radical of the formula $NR^{14}R^{15}$, $(C_3-C_6)$ cycloalkyl, $(C_2-C_4)$alkenyl, $(C_2-C_4)$alkynyl, $(C_3-C_4)$alkenyloxy or $(C_3-C_4)$ alkynyloxy, Z is CH or N, $R^{14}$ and $R^{15}$ independently of one another are H, $(C_1-C_3)$alkyl or $(C_3-C_4)$alkenyl, $X^1$ is $CH_3$, $OCH_3$, $OC_2H_5$ or $OCHF_2$, $Y^1$ is —O— or —$CH_2$, $X^2$ is $CH_3$, $C_2H_5$ or $CH_2CF_3$, $Y^2$ is $OCH_3$, $OC_2H_5$, $SCH_3$, $SCH_2CH_3$, $CH_3$ or $C_2H_5$, $X^3$ is $CH_3$ or $OCH_3$, $Y^3$ is H or $CH_3$, $X^4$ is $CH_3$, $OCH_3$, $OC_2H_5$, $CH_2OCH_3$ or Cl, $Y^4$ is $CH_3$, $OCH_3$, $OC_2H_5$ or Cl, and $Y^5$ is $CH_3$, $C_2H_5$, $OCH_3$ or Cl, MCPA, 2,4-D, bromoxynil, bentazone, fluthiacet, pyridate, diflufenzopyr, carfentrazone, clopyralid, halosulfuron, thifensulfuron, prosulfuron, iodosulfuron, tritosulfuron, sulfosulfuron, 2,4-D, MCPA, bensulfuron, methsulfuron, acifluorfen, bispyribac, ethoxysulfuron, cinosulfuron, pyrazosulfuron, imazosulfuron, cyclosulfamuron, chlorsulfuron, bromobutide, bentazone, benfuresate, chlorimuron, diflufenican, flurtamone, tribenuron, amidosulfuron, mecoprop/mecoprop-p, dichlorprop/dichlorprop-P, fluroxypyr, picloram, loxynil, bifenox, pyraflufen-ethyl, fluoroglycofen-ethyl, cinidon-ethyl, picolinofen, glufosinate, glyphosate, imazapyr, imazethapyr, imazamethabenz, imazamethabenz-methyl, imazamox, imazaquin and imazapic.

2. The herbicide combination as claimed in claim 1, wherein, as component (A), one or more compounds of the formula (A1) or their salts,

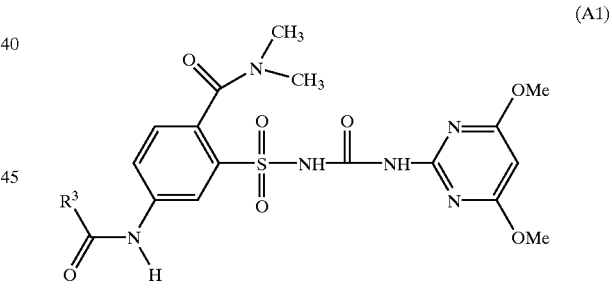

(A1)

in which $R^3$ is H, $(C_1-C_4)$alkyl, $(C_1-C_4)$alkoxy, $(C_2-C_4)$ alkenoxy, $(C_2-C_4)$alkynoxy, $(C_3-C_6)$cycloalkyl, each of the 5 last-mentioned radicals being unsubstituted or substituted by one or more radicals from the group consisting of halogen, cyano, $(C_1-C_4)$alkoxy and $(C_1-C_4)$alkylsulfonyl, and Me=methyl.

3. The herbicide combination as claimed in claim 1, which comprises at least two B compounds, additives customary in crop protection and formulation auxiliaries.

4. A method of controlling harmful plants which comprises applying the herbicides of the herbicide combination, as defined in claim 1, jointly or separately, pre-emergence, post-emergence or pre- and post-emergence to the plants, parts of the plants, seeds of the plants or the area under cultivation.

5. The method as claimed in claim 4 for selective control of harmful plants in plant crops.

6. The method as claimed in claim 5 for the control of harmful plants in cereals.

7. A method of controlling harmful plants comprising applying the herbicide combination as defined in claim 2 to the harmful plants or to an area where the harmful plants reside.

8. The method of claim 6, wherein the cereal is corn.

9. A synergistic herbicide combination comprising a synergistic effective amount of component (A) and component (B), wherein component (A) is selected from (A1) having the formula (A1) or their salts,

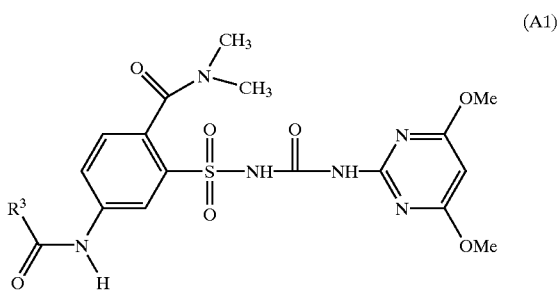

in which $R^3$ is H, $(C_1-C_4)$alkyl, $(C_1-C_4)$alkoxy, $(C_2-C_4)$alkenoxy, $(C_2-C_4)$alkynoxy, $(C_3-C_6)$cycloalkyl, each of the 5 last-mentioned radicals being unsubstituted or substituted by one or more radicals from the group consisting of halogen, cyano, $(C_1-C_4)$ alkoxy and $(C_1-C_4)$alkylsulfonyl, and Me=methyl, and component (B) is selected from atrazine, metolachlor, bromoxynil, pyridate, iodosulfuron-methyl, glufosinate-ammonium and the monoammonium salt, nicosulfuron, rimsulfuron, halosulfuron, sulcotrione, glyphosate-isopropylammonium, primisulfuron, metribuzin, mesotrione, syanazine, dimethenamid, fluthiamide, metosulam, MCPA, alachlor, acetochlor, isoxachlortole, clopyralid, dicamba, imazethapyr, sethoxydim, diclofop/diclofop-P, fenoxaprop/fenoxaprop-P or its esters, ethoxysulfuron, anilofos, amidosulfuron, prosulfuron, dichlorprop, linuron, terbutylazine, fluroxypyr, 2,4-D, tribenuron, methsulfuron, thifensulfuron, imazamox, and carfentrazone.

10. The herbicide combination of claim 9, wherein component (A) is N-(N-4,6-Dimethyoxypyrimidin-2-yl) aminocarbonyl)-2-(dimethylaminocarbonyl)-5-(formylamino)-benzenesulfonamide or a combination of N-(N-4,6-Dimethyoxypyrimidin-2-yl)aminocarbonyl)-2 (dimethylaminocarbonyl)-5-(formylamino)-benzenesulfonamide and ethyl 5,5-diphenyl-2-isoxazolinecarboxylate.

11. The herbicide combination of caim 10, wherein component (A) is N-(N-4,6-Dimethyoxypyrimidin-2-yl) aminocarbonyl)-2-(dimethylaminocarbonyl)-5-(formylamino)-benzenesulfonamide and component (B) is atrazine, metolachlor, bromoxynil, pyridate, iodosulfuron-methyl, glufosinate-ammonium and the monoammonium salt, nicosulfuron, rimsulfuron, halosulfuron, sulcotrione, glyphosate-isopropylammonium, primisulfuron, metribuzin, mesotrione, syanazine, dimethenamid, fluthiamide, metosulam, MCPA, alachlor, acetochlor, dicamba, diclofop/diclofop-P, fenoxaprop/fenoxaprop-P or its esters, ethoxysulfuron, anilofos, or amidosulfuron.

12. The herbicide combination of claim 10, wherein component (A) is a combination of N-(N-4,6-Dimethyoxypyrimidin-2-yl)aminocarbonyl-2-(dimethylaminocarbonyl)-5-(formylamino)-benzenesulfonamide and ethyl 5,5-diphenyl-2-isoxazolinecarboxylate and component (B) is atrazine, iodosulfuron-methyl, isoxachlortole, clopyralid, imazethapyr, sethoxydim, prosulfuron, dichlorprop, dicamba, linuron, terbutylazine, fluroxypyr, 2,4-D, tribenuron, methsulfuron, flumetsulan thifensulfuron, imazamo, or carfentrazone.

13. The herbicide combination of claim 12, wherein the combination further comprises diflufenzopyr when component (B) is dicamba.

14. The herbicide combination of claim 12, wherein the combination further comprises metolachlor when component (B) is flumetsulam.

* * * * *

UNITED STATES PATENT AND TRADEMARK OFFICE
CERTIFICATE OF CORRECTION

PATENT NO.    : 6,486,096 B1
DATED         : November 26, 2002
INVENTOR(S)   : Hacker et al.

It is certified that error appears in the above-identified patent and that said Letters Patent is hereby corrected as shown below:

<u>Column 41,</u>
Line 46, delete "syanazine" and insert -- cyanazine --.

<u>Column 45,</u>
Line 33, add the words -- iodosulfuron-methyl sodium --.

<u>Column 46,</u>
Lines 17 and 30, add the words -- iodosulfuron-methyl sodium --.

Signed and Sealed this

Seventeenth Day of June, 2003

JAMES E. ROGAN
*Director of the United States Patent and Trademark Office*